US011389405B2

(12) United States Patent
Gu et al.

(10) Patent No.: US 11,389,405 B2
(45) Date of Patent: Jul. 19, 2022

(54) ARTIFICIAL BETA CELLS AND METHODS OF USE THEREOF

(71) Applicant: NORTH CAROLINA STATE UNIVERSITY, Raleigh, NC (US)

(72) Inventors: Zhen Gu, Los Angeles, CA (US); Zhaowei Chen, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 0 days.

(21) Appl. No.: 16/648,026

(22) PCT Filed: Sep. 17, 2018

(86) PCT No.: PCT/US2018/051310
§ 371 (c)(1),
(2) Date: Mar. 17, 2020

(87) PCT Pub. No.: WO2019/055901
PCT Pub. Date: Mar. 21, 2019

(65) Prior Publication Data
US 2020/0253869 A1 Aug. 13, 2020

Related U.S. Application Data

(60) Provisional application No. 62/559,909, filed on Sep. 18, 2017.

(51) Int. Cl.
A61K 9/127 (2006.01)
A61K 38/28 (2006.01)
A61K 47/42 (2017.01)

(52) U.S. Cl.
CPC ............. A61K 9/127 (2013.01); A61K 38/28 (2013.01); A61K 47/42 (2013.01)

(58) Field of Classification Search
CPC ........ A61K 9/127; A61K 38/28; A61K 47/42; A61K 47/6911
See application file for complete search history.

(56) References Cited

U.S. PATENT DOCUMENTS 3,984,532 A * 10/1976 Fernandez de Castro .................. C12Q 1/37
435/7.4
5,690,956 A * 11/1997 Lau .......................... A61K 8/55
424/450

(Continued)

FOREIGN PATENT DOCUMENTS

CN 101528197 A 9/2009
WO 2016/172320 A1 10/2016

OTHER PUBLICATIONS

Tournois, H., et al in Biochemistry, vol. 29, pp. 8297-8307, 1990.*
(Continued)

Primary Examiner — Gollamudi S Kishore
(74) Attorney, Agent, or Firm — Meunier Carlin & Curfman LLC

(57) ABSTRACT

Disclosed herein is a particle containing an inner liposomal vesicle (ILV) encapsulating a therapeutic agent; an outer liposomal vesicle (OLV) encapsulating the ILV; a membrane fusion-promoting agent; and a pH-altering agent. Also disclosed are methods of delivering a therapeutic agent to a subject comprising: a) providing a herein disclosed particle b) triggering ILV and OLV fusion; and c) releasing the therapeutic agent outside of the OLV. Also disclosed are methods for treating a disease in a subject in need thereof comprising: administering to a subject a herein disclosed particle. Also disclosed are methods to release insulin to an environment comprising increased glucose levels, the method comprising exposing to the environment a herein disclosed particle.

19 Claims, 28 Drawing Sheets

(56) References Cited

U.S. PATENT DOCUMENTS

| | | | |
|---|---|---|---|
| 6,200,599 B1* | 3/2001 | Nantz | A61P 19/08 424/450 |
| 7,273,620 B1 | 9/2007 | Zhigaltsev et al. | |
| 2002/0061331 A1* | 5/2002 | Zasadzinski | A61K 9/1277 424/451 |
| 2003/0125517 A1* | 7/2003 | Cullis | C07K 7/08 530/324 |
| 2008/0175895 A1* | 7/2008 | Kogure | C12Y 111/01006 424/450 |
| 2009/0285880 A1 | 11/2009 | Hellerbrand et al. | |
| 2012/0321683 A1* | 12/2012 | De La Maza Rivera | A61K 9/127 424/401 |
| 2015/0150801 A1 | 6/2015 | Park et al. | |
| 2016/0130216 A1* | 5/2016 | Yousaf | C07C 239/20 424/450 |
| 2017/0190798 A1* | 7/2017 | Jing | G01N 33/48721 |
| 2020/0239367 A1* | 7/2020 | Huth | E04B 1/942 |

OTHER PUBLICATIONS

Lachaal, M., et al in BBA, vol. 1466, #1-2, pp. 379-389, 2000.*

Leturque. A., et al Am J Physiol Endocrinol Metab., vol. 296, E985-E992, 2009.*

Kisak, E.T. et al, Current Medicinal Chemistry, vol. 11, 199-219, 2004.*

Scheepers A., et al, Journal of Parenteral and Enternal Nutrition, vol. 28, # 5, pp. 364-371, 2004.*

International Search Report and Written Opinion, issued in corresponding application No. PCT/US2018/051310, dated Jan. 4, 2019, 11 pages.

Niu et al. "Liposomes Containing Glycocholate as Potential Oral Insulin Delivery Systems: Preparation, in vitro Characterization, and Improved Protection Against Enzymatic Degradation," International Journal of Nanomedicine, Jun. 7, 2011 (Jun. 7, 2011), vol. 6.

Chen et al. "Synthetic Beta Cells for Fusion-Mediated Dynamic Insulin Secretion," Nature Chemical Biology. Oct. 30, 2017 {Oct. 30, 2017), vol. 14, Iss. 1.

Liu et al. "Self-assembled lecithin/chitosan nanoparticles for oral insulin delivery: preparation and functional evaluation," International Journal of Nanomedicine, Feb. 24, 2016 (Feb. 24, 2016), vol. 11.

Chong-Kook Kim et al., "Development of glucose-triggered pH-sensitive liposomes for a potential insulin delivery," International Journal of Pharmaceutics, vol. 101, pp. 191-197, Dec. 31, 1994.

Hana Robson Marsden et al., "Controlled liposome fusion mediated by SNARE protein mimics," Biomaterials Science, No. 1, pp. 1046-1054, Dec. 31, 2013.

Huang Linjing et al., "Research Progress of the Relationship between Glucose Transporter 2 and Diabetes," Medical Recapitulate, vol. 15, No. 23, pp. 3617-3619, Dec. 31, 2009.

Ramya H. Tunuguntla et al., "Ultrafast proton transport in sub-1-nm diameter carbon nanotube porins," Nature Nanotechnology, vol. 11, pp. 639-644, Jul. 31, 2016.

Qi Wei, Preparation of glucose-responsive protein microcapsules and application thereof as drug carriers), Abstracts of Papers of the 13th Colloid and Interface Chemistry Conference of the Chinese Chemical Society, p. 402, Jul. 20, 2011.

First Office Action issued in corresponding Chinese application No. 201880074639.0, dated Nov. 25, 2021.

* cited by examiner

ARTIFICIAL BETA CELLS AND METHODS OF USE THEREOF

CROSS REFERENCE TO RELATED APPLICATIONS

This is a national stage application of PCT International Application No. PCT/US2018/051310, filed on Sep. 17, 2018, entitled "ARTIFICIAL (β-CELLS AND METHODS OF USE THEREOF," which claims priority to, and the benefit of U.S. Provisional Patent Application Ser. No. 62/559,909, filed Sep. 18, 2017, the disclosures of which are expressly incorporated herein by reference in their entireties.

FIELD

The disclosure herein relates to particles, methods for delivering a therapeutic agent, and methods for treating a disease (e.g., diabetes).

BACKGROUND

Pancreatic β-cells dynamically regulate insulin secretion to maintain blood glucose homeostasis. Destruction or dysfunction of these cells leads to type 1 and type 2 diabetes mellitus, a family of chronic diseases that currently affect over 415 million people in the world (Rorsman, P., Annu. Rev. Physiol. 75, 155-179 (2013); Yu, J. et al., Proc. Natl Acad. Sci. USA 112, 8260-8265 (2015); Ohkubo, Y. et al., Diabetes. Res. Clin. Pract. 28, 103-117 (1995)). Inadequate glucose control caused by loss of β-cell function can lead to hyperglycemia, which is directly implicated in the development of severe complications, including blindness, renal failure and cardiovascular disease (Nathan, D., New Engl. J. Med. 328, 1676-1685 (1993)). On the other hand, traditional intensive insulin therapy by periodic injections imperfectly simulates the dynamics of β-cells and can cause hypoglycemia, which is associated with risks of behavioral and cognitive disturbance, brain damage, or death (Nathan, D., Diabetes Care 37, 9-16 (2014); Control, T. et al., New Engl. J. Med. 329, 977-986 (1993); Orchard, T. et al., JAMA 313, 45-53 (2015)). Cell therapy is gathering momentum as a promising strategy for restoring tight glycemic control while mitigating episodes of both hyper- and hypoglycemia in patients with diabetes (Xie, M. et al., Science 354, 1296-1301 (2016); Pepper, A. et al., Nat. Biotech. 33, 518-523 (2015); Vegas, A. J. et al., Nat. Med. 22, 306-311 (2016)). Yet this approach is limited by the shortage of donor islets and the requirement for immunosuppression after transplantation (Veiseh, O. et al., Nat. Rev. Drug. Discov. 14, 45-57 (2015)).

As an alternative to the use of living cells for therapeutic purposes, a variety of biomimetic assemblies have been proposed to recreate the key functions of cells (Zhang, Y. et al., Trends Biotechnol. 26, 14-20 (2008); Szostak, J. et al., Nature 409, 387-390 (2001)). Prominent examples of complex assemblies include cell membrane-cloaked nanoparticles, deformable microgels and vesicles with integrated proteins for detoxification, vaccines, haemostasis and drug release (Hu, C. et al., Nat. Nano. 8, 933-938 (2013); Hu, C. et al., Nature 526, 118-121 (2015); Brown, A. C. et al., Nat. Mater. 13, 1108-1114 (2014); Hu, Q. et al., Adv. Mater. 28, 9573-9580 (2016); Molinaro, R. et al., Nat. Mater. 15, 1037-1046 (2016)). All of these assemblies can be viewed as single-compartment structures, and their interactions with biological entities are relatively passive compared to those exhibited by 'living' cells. Although multi-compartmentalized assemblies have been created to reconstitute the hierarchical architecture of cells for delivering drug cocktails or conducting cascade reactions (Boyer, C. et al., ACS Nano 1, 176-182 (2007); Wong, B. et al., Adv. Mater. 23, 2320-2325 (2011); Marguet, M. et al., Angew. Chem. Int. Ed. 51, 1173-1176 (2012); Peters, R. et al., Angew. Chem. Int. Ed. 53, 146-150 (2014); Elani, Y. et al., Nat. Commun. 5, 5305-5309 (2014); Chiu, H. et al., Angew. Chem. Int. Ed. 47, 1875-1878 (2008)), replication of "sense-react" behaviors of natural cells remains elusive. Indeed, a key challenge in the de novo design of synthetic therapeutic cells is to mimic the higher-order functions of their natural counterparts that can precisely sense the external environment, make an internal decision, and release feedback (Zhang, Y. et al., Trends Biotechnol. 26, 14-20 (2008); Lu, Y., et al., Nat. Rev. Mater. 1, 16075 (2016)), a process routinely employed by pancreatic β-cells in response to changes in glycemic levels.

Like other biomolecule-secreting cells, β-cells can export cellular cargos to the outside through a vesicle transport system and a membrane fusion process upon external stimulation (Hata, Y., et al., Nature 366, 347-351 (1993); Kaiser, C. et al., Cell 61, 723-733 (1990); Sollner, T. et al., Nature 362, 318-324 (1993)).

The compositions and methods disclosed herein address these and other needs.

SUMMARY

Disclosed herein is a novel particle having a sense-and-response system for the delivery of a therapeutic agent (e.g., insulin).

Disclosed herein is a particle comprising: an inner liposomal vesicle (ILV) encapsulating a therapeutic agent; an outer liposomal vesicle (OLV) encapsulating the ILV; a membrane fusion-promoting agent; and a pH-altering agent. In some aspects, the therapeutic agent is insulin. In some aspects, the membrane fusion-promoting agent promotes fusion between the ILV and the OLV. In some aspects, the pH-altering agent comprises a glucose-responsive enzyme. In some aspects, the ILV further comprises a membrane fusion-inhibiting agent which shields access to the membrane fusion-promoting agent.

Also disclosed herein are methods of delivering a therapeutic agent to a subject comprising: a) providing a particle comprising an inner liposomal vesicle (ILV) encapsulating a therapeutic agent, an outer liposomal vesicle (OLV) encapsulating the ILV, a membrane fusion-promoting agent, and a pH-altering agent; b) triggering ILV and OLV fusion; and c) releasing the therapeutic agent outside of the OLV. In some aspects, the triggering step b) is facilitated by binding of the membrane fusion-promoting agent. In some aspects, the releasing c) is facilitated in hyperglycemic conditions. In some aspects, the releasing c) is inhibited in hypoglycemic conditions.

Also disclosed herein are methods of treating a disease in a subject in need thereof comprising: administering to a subject a particle comprising an inner liposomal vesicle (ILV) encapsulating a therapeutic agent, an outer liposomal vesicle (OLV) encapsulating the ILV, a membrane fusion-promoting agent, and a pH-altering agent. In some aspects, the disease is diabetes. In some aspects, the particle treats hyperglycemia and avoids inducing hypoglycemia.

BRIEF DESCRIPTION OF THE DRAWINGS

The accompanying figures, which are incorporated in and constitute a part of this specification, illustrate several aspects described below.

DNA1 (labeled with DNA-donor)/DNA2 (labeled with DNA acceptor)-cholesterol-inserted ISVs at pH 7.4 and pH 5.5 with excitation at 555 nm. See Table 1 for DNA sequence details. (c) and (d), respectively showed the fluorescence intensity of DNA-donor in (a) and (b) at different cycles of switching pH at 7.4 and 5.5. The fluorescence intensity at each cycle was measured 20 min after switching the pH. Data points represent mean±SD (n=3).

Figure 9:
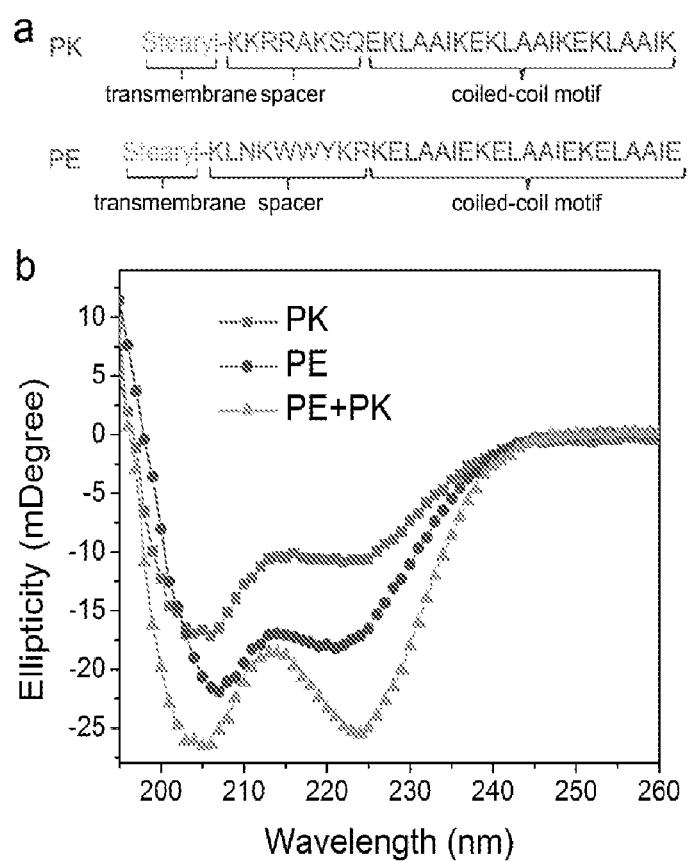

FIG. 9 shows a, sequences of peptide-K and peptide-E with three components-a transmembrane domain, a spacer and a recognition motif, mimicking the membrane fusion SNARE polypeptides (SNARE=soluble NSF attachment protein receptor). The sequences were designed by modifying previously reported peptides. b, CD spectra of peptide-E, peptide-K, and peptide-E/peptide-K. Peptide-K shows substantial α-helical content in CD spectra ($[\theta]_{220\ nm}/[\theta]_{208\ nm}$ is ~0.71), whereas peptide-E adopts a predominantly random coil structure. After mixing, the α-helix content increases as the ratio of $[\theta]_{220\ nm}/[\theta]_{208\ nm}$ is about 1, confirming the formation of coiled-coil structures between peptide-E and peptide-K.

Figure 10:
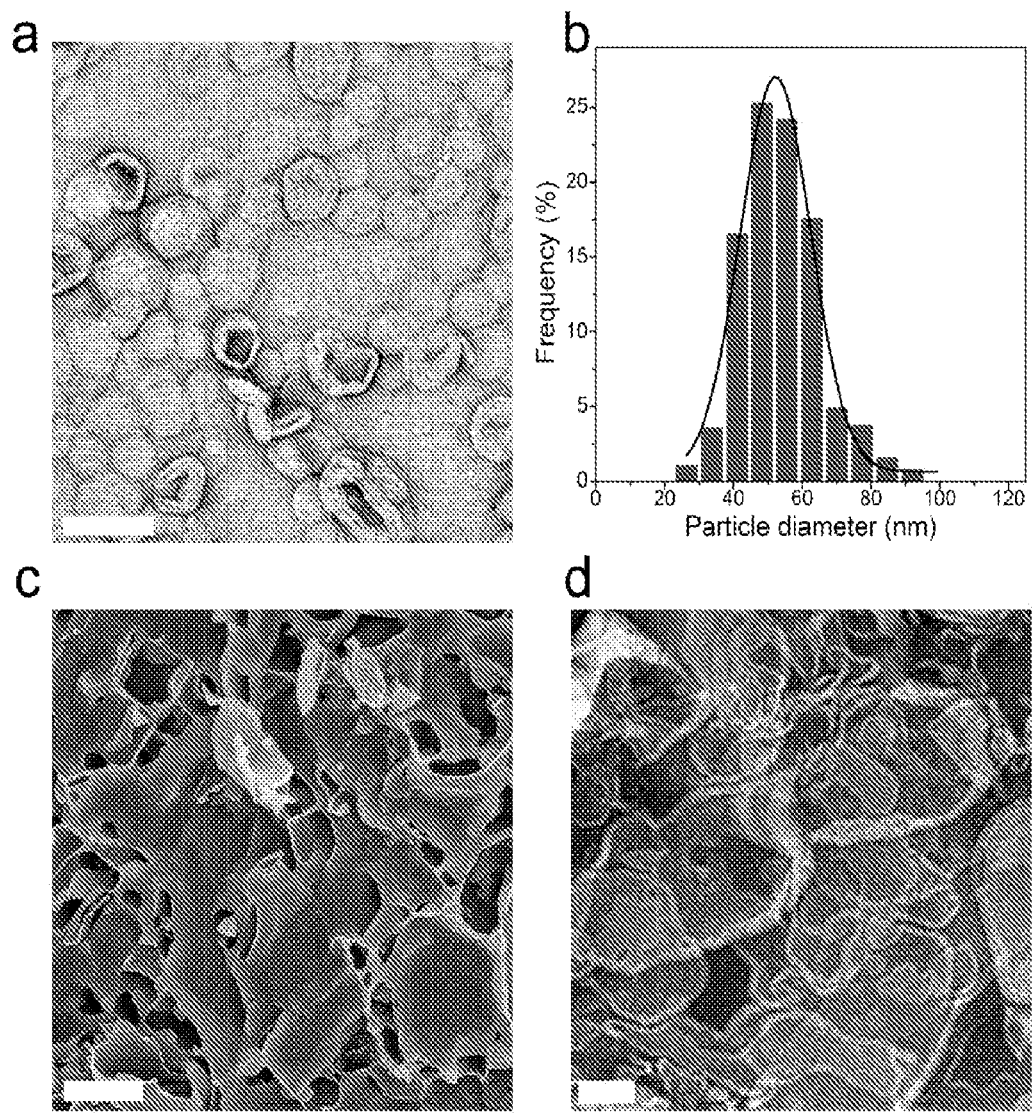

FIG. 10 shows a, Transmission electron microscopy image (TEM) of the DPPC liposomes (scale bar, 100 nm); b, Size distribution histogram of the liposomes shown in panel a; cryogenic scanning electron microscopy (c) and TEM (d) of the interdigitated bilayer sheets made from the DPPC liposomes (c scale bar, 2 μm; d scale bar, 100 nm).

Figure 11:
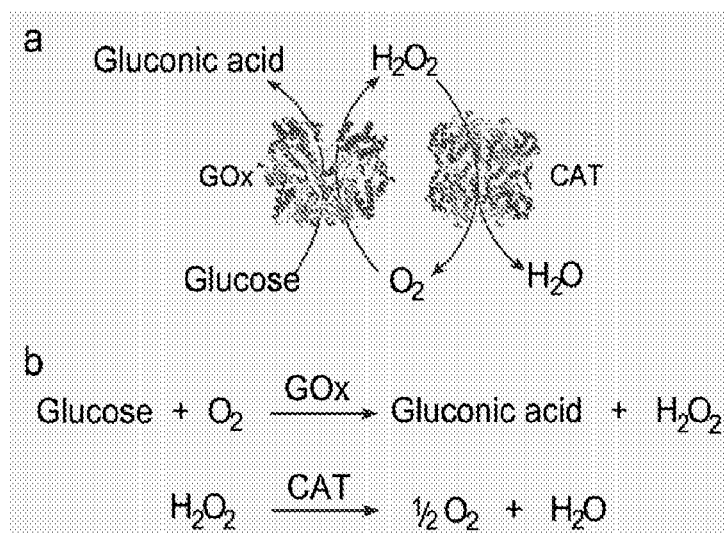

FIG. 11 shows (a) Schematic illustration and (b) reaction equations of the enzymatic reactions involving glucose oxidation catalyzed by glucose oxidase (GOx) and hydrogen peroxide breakdown by catalase (CAT). The decomposition of the undesired hydrogen peroxide can regenerate oxygen to facilitate glucose oxidation.

Figure 12:
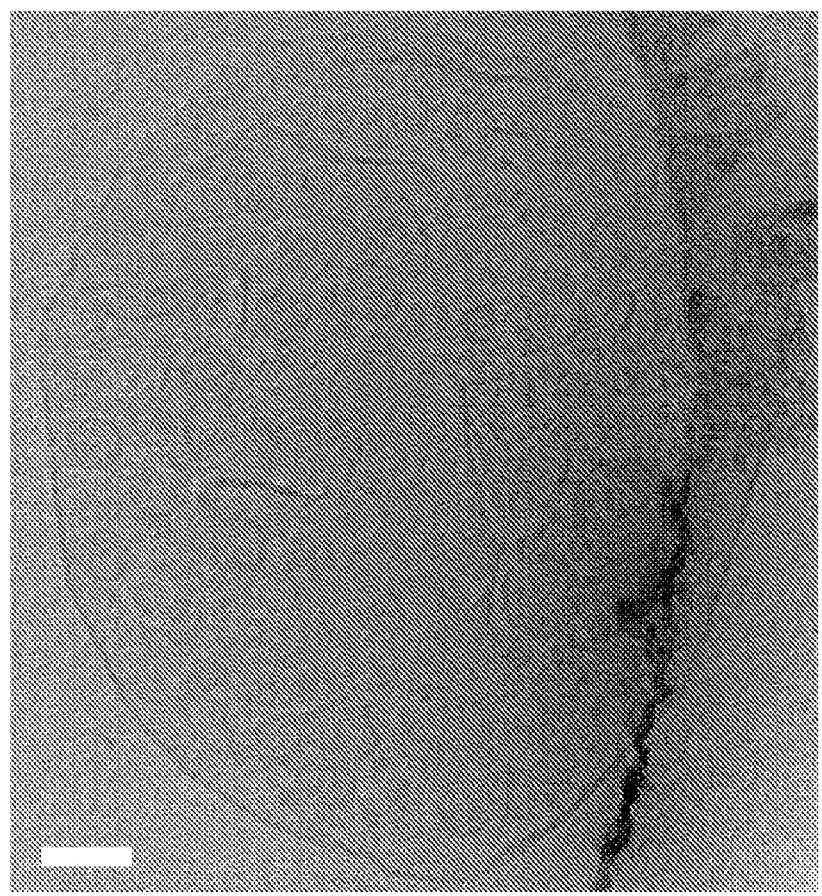

FIG. 12 is a representative cryogenic transmission electron microscopy (cryoTEM) image of the final vesicles-in-vesicle superstructures. Scale bar: 100 nm.

Figure 1:
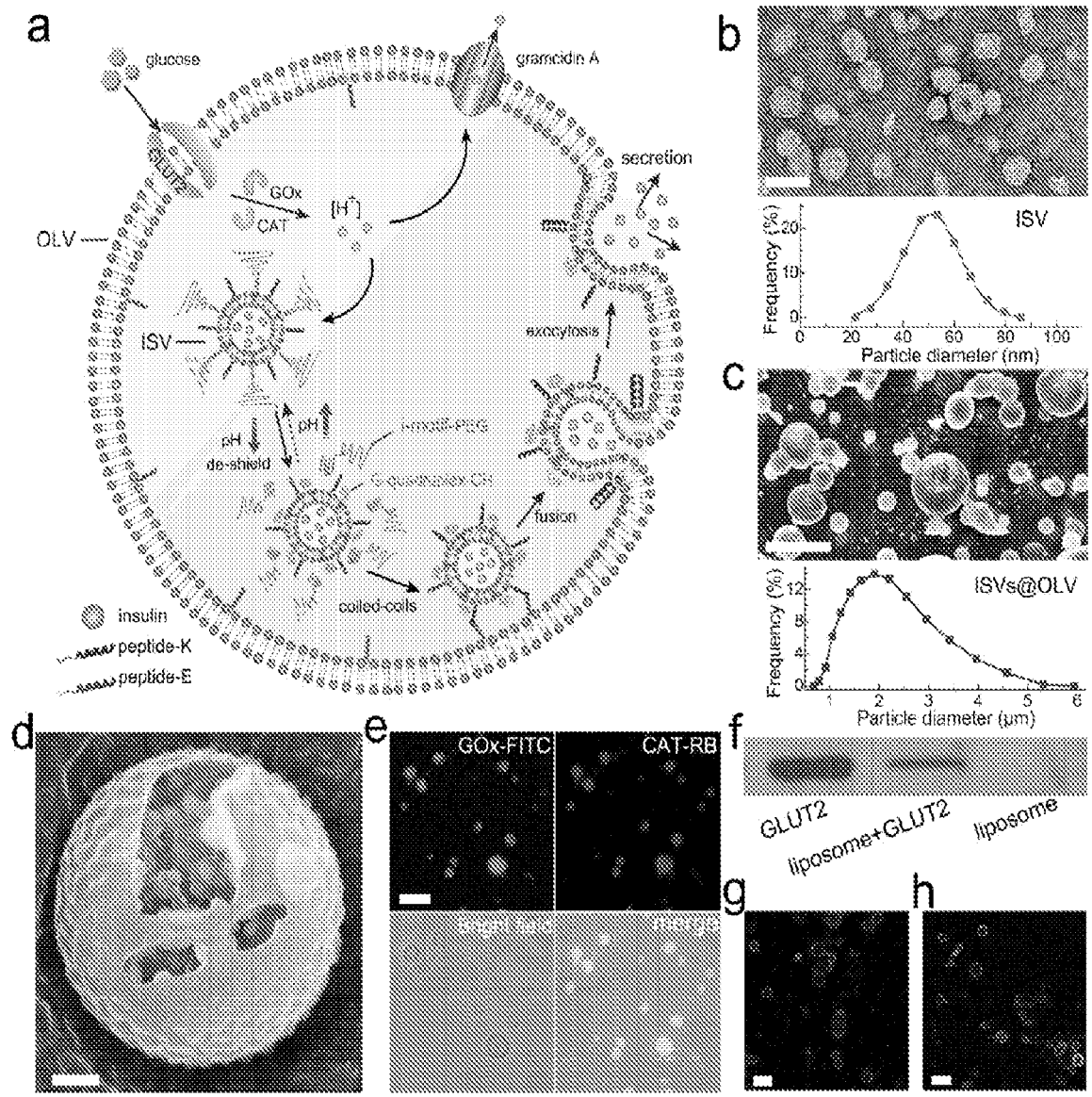
FIG. 1 shows the design and synthesis of the artificial β-cell (AβC). GLUT2, GOx and CAT are abbreviations for glucose transporter 2, glucose oxidase, and catalase, respectively. a, Schematic summation of the biochemical processes inside the AβCs. b, (Top) The inner small liposomal vesicles (ISVs), stained with uranyl-acetate and imaged by transmission electron microscopy, were used to mimic insulin granules inside natural β cells (scale bar, 100 nm). (Bottom) showed the size distribution histogram of the insulin-containing ISVs. c, Cryo-SEM (Top) and size distribution (Bottom) and d, magnified fractured cryo-SEM of the vesicles-in-vesicle superstructures (scale bar in c, 5 μm; scale bar in d, 200 nm). From the fracture in panel d, small liposomal vesicles can be clearly seen inside the large liposome. e, Confocal laser microscopy image (CLSM) to verify the encapsulation of glucose oxidase labeled with fluorescein isothiocyanate (GOx-FITC) and catalase labeled with rhodamine B (CAT-RB) inside the large liposomes (scale bar, 5 am). f, Western blotting results indicating the retention of immunoreactivity of glucose transporter 2 (GLUT2) in the superstructures. g, CLSM image showing the reconstitution of GLUT2 labeled with RB on the membranes of the larger liposomes (scale bar, 5 μm). h, CLSM image to demonstrate the insertion of the proton channel gramicidin A labeled with lysine-5-carboxyfluorescein into the outer membrane (scale bar, 5 μm).
Figure 13:
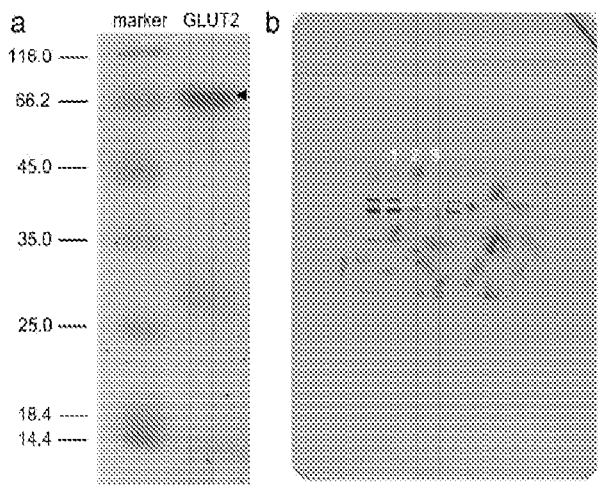

FIG. 13 shows (a) SDS-PAGE analysis of the purified glucose transporter 2 (GLUT2). (b) Uncropped western blots for FIG. 1f. Lanes used for FIG. 1f are indicated by a rectangle, where Lane 1, 2 and 3 respectively represent the blots of GLUT2, liposomal superstructures inserted with GLUT2, and pure liposomal superstructures. The lanes on the left side of lane 1 and right side of lane 3 are GLUT2 isolated from different batches of bacteria.

Figure 14:
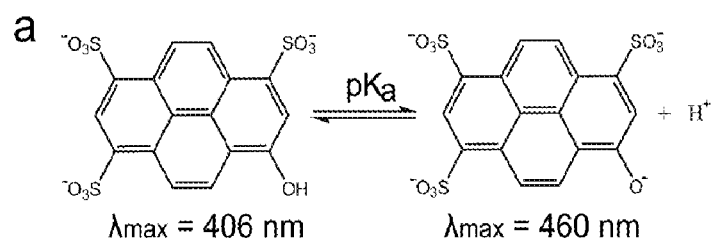
Figure 14:
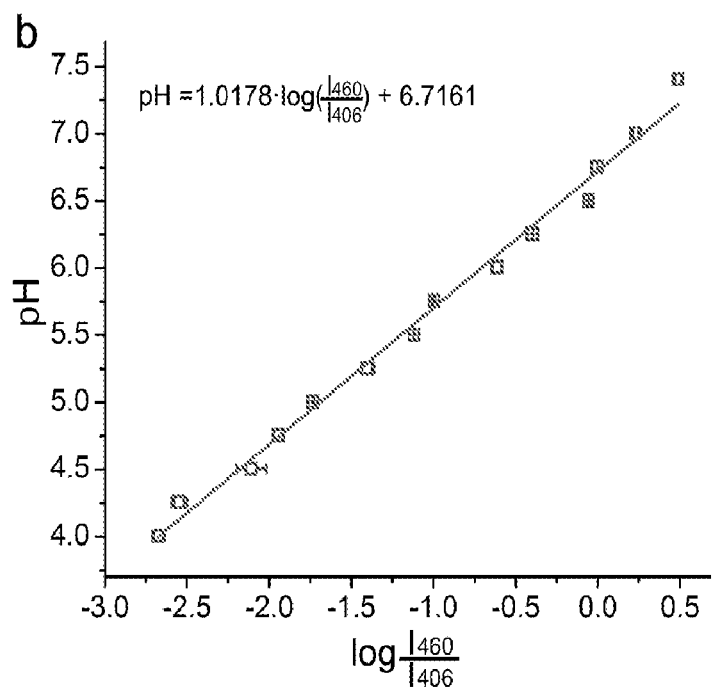

FIG. 14 shows a, Unionized and ionized forms of HPTS ($pK_a$=7.2). b, pH titrations of the relative fluorescence intensities of HPTS excited at 406 nm and 460 nm (HEPES buffer, 5 mM, 100 mM NaCl). The fluorescence intensities of HPTS at 514 nm excited by 406 ($I_{406}$) and 460 ($I_{460}$) nm were strongly dependent on the degree of ionization of the 8-hydroxyl group and hence on the medium pH. Data points represent mean±SD (n=3).

Figure 15:
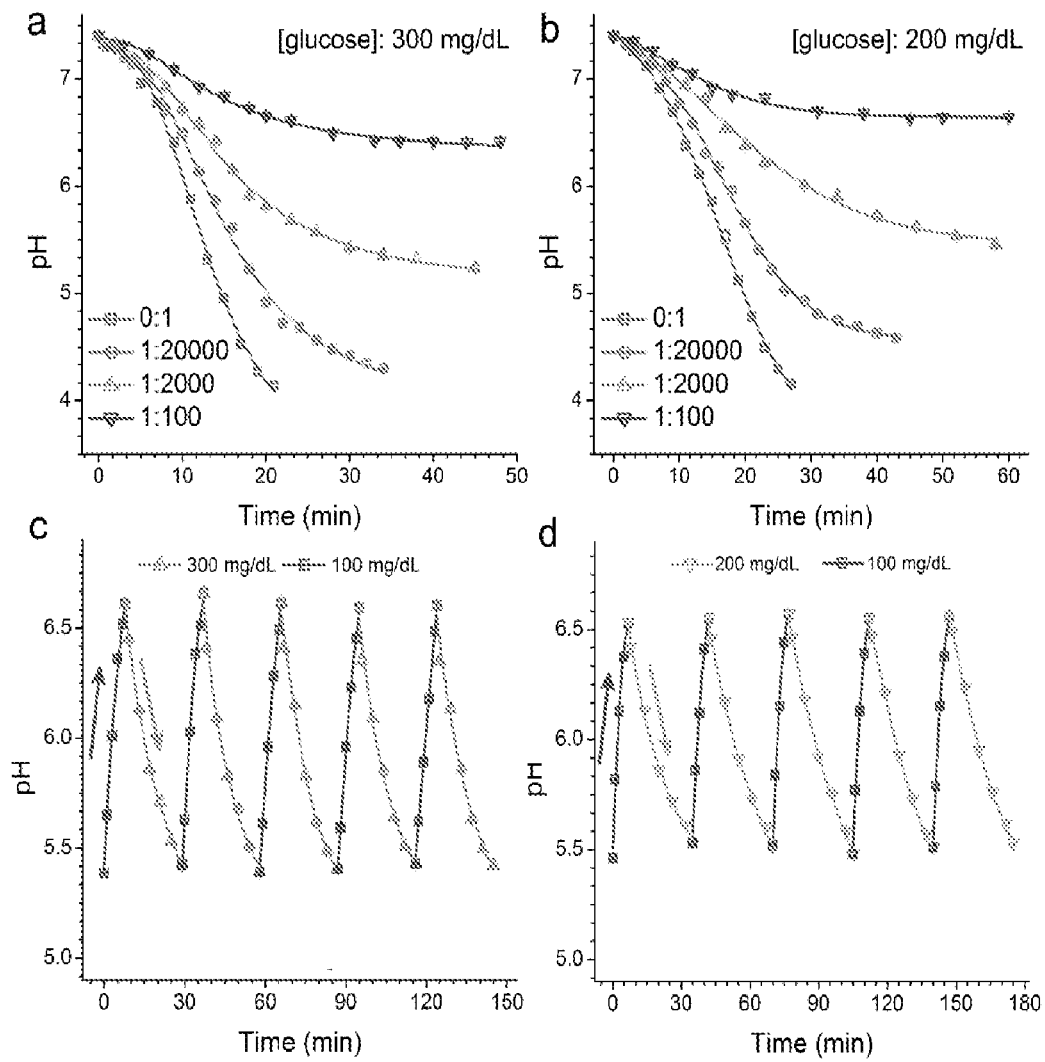

FIG. 15 is a set of graphs depicting pH variation inside AβCs at modest glucose concentrations with different gramicidin insertion in (a) 300 mg/dL and (b) 200 mg/dL glucose solutions. The ratio in the figure label indicates the ratio of gramicidin-to-dipalmitoylphosphatidylcholine lipid. c, d, Reversible pH variation as a result of alternatively switching environmental glucose concentrations. Data points represent mean±SD (n=3).

Figure 16:
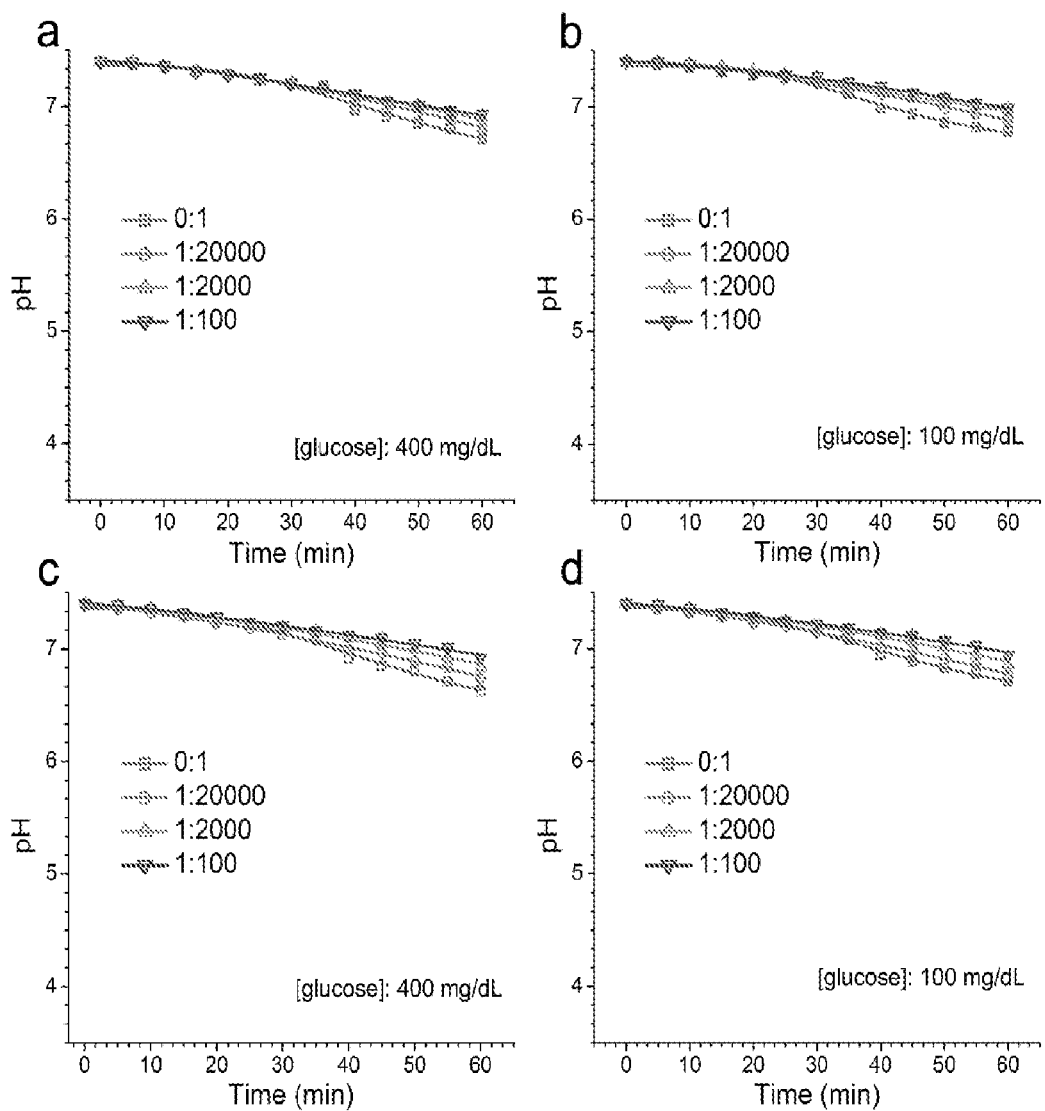

FIG. 16 is a set of graphs depicting pH changes inside control AβCs with no glucose transporter 2 reconstitution in (a) 400 md/dL and (b) 100 mg/dL glucose solutions, and glucose transporter 2 inhibitor-Cytochalasin B pre-treated AβCs in (c) 400 md/dL and (d) 100 mg/dL glucose solutions. The ratios in the figure represent the molar ratio of the added GA-to-lipid of the outer large liposomal vesicles. In all the control groups, no significant pH variation was observed compared to their counterparts in the experimental group over the same time. The slower decrease in pH is likely induced by the passive diffusion of glucose into the control AβCs. These results show glucose transporter 2 was responsible for the uptake of glucose into AβC, in which subsequent glucose oxidation induced pH variation. Data points represent mean±SD (n=3).

Figure 17:
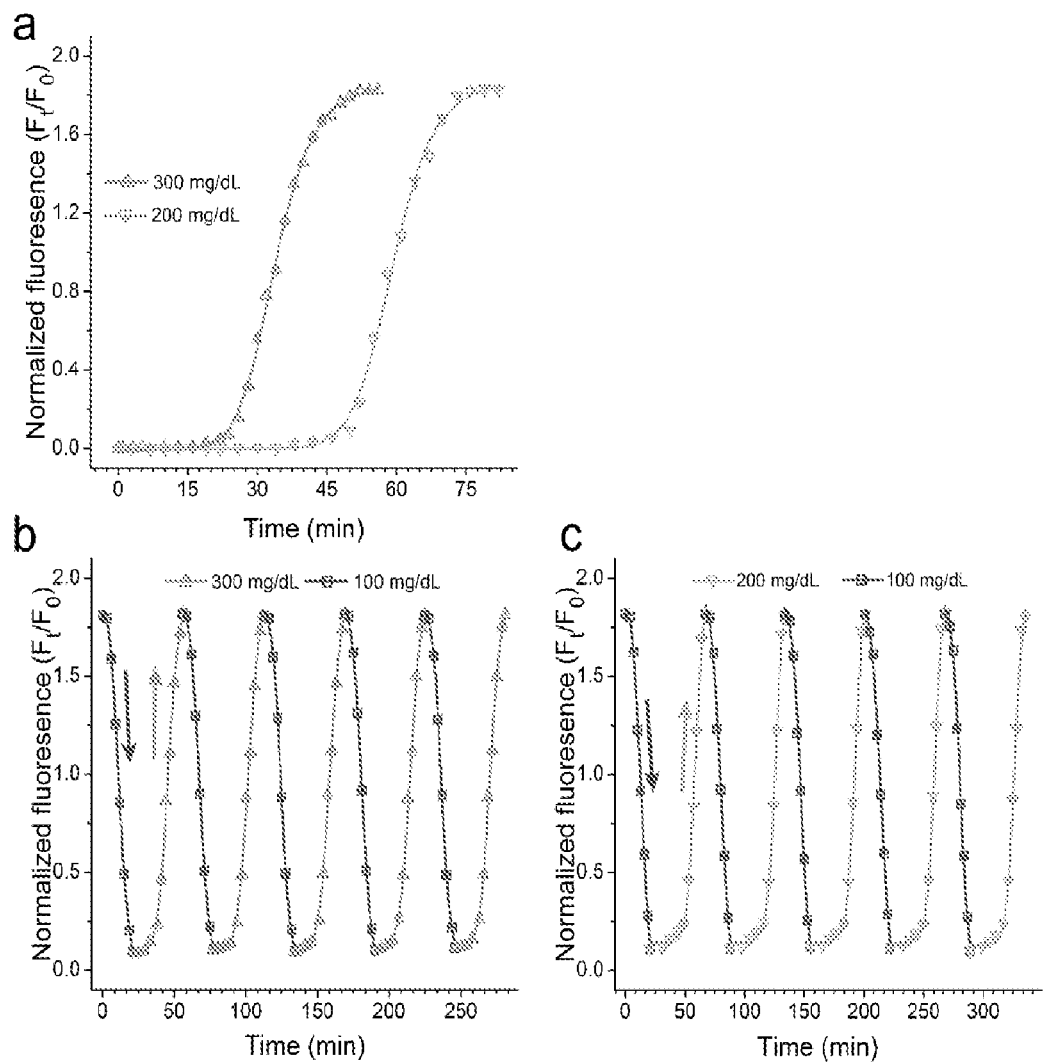

FIG. 17 shows a, FRET assay to study the dehybridization of the pH-sensitive DNA duplex which bridges the PEG shield and the ISV surface, accompanying the glucose metabolism by AβCs in 300 mg/mL and 200 mg/mL glucose solutions. $F_0$ and $F_t$ represent the fluorescence intensity measured before and at time t after addition into glucose solutions. b and c, Reversible quenching and recovery of the fluorescence of DNA-donor to demonstrate the reversible attachment and detachment of the PEG shield at high and low glucose solutions. Data points represent mean±SD (n=3).

Figure 18:
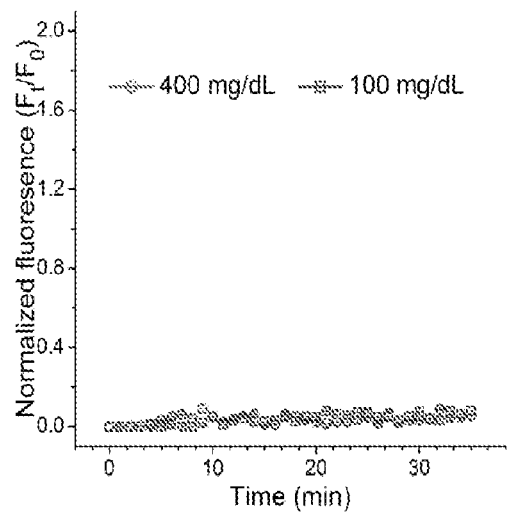

FIG. 18 is a graph depicting a FRET assay to study the dehybridization of the non-pH-sensitive DNA duplex which bridges the PEG shield and the ISV surface, accompanying the glucose metabolism by AβCs in 400 mg/mL and 100 mg/mL glucose solutions. $F_0$ and $F_t$ represent the fluorescence intensity measured before and at time t after addition into glucose solutions. The results demonstrated that no disassociation of the control duplex DNA occurred at either high or low glucose levels due to the lack of pH-sensitive properties. The fluorophore and quencher modification information was shown in Table 1. Data points represent mean±SD (n=3).

Figure 19:
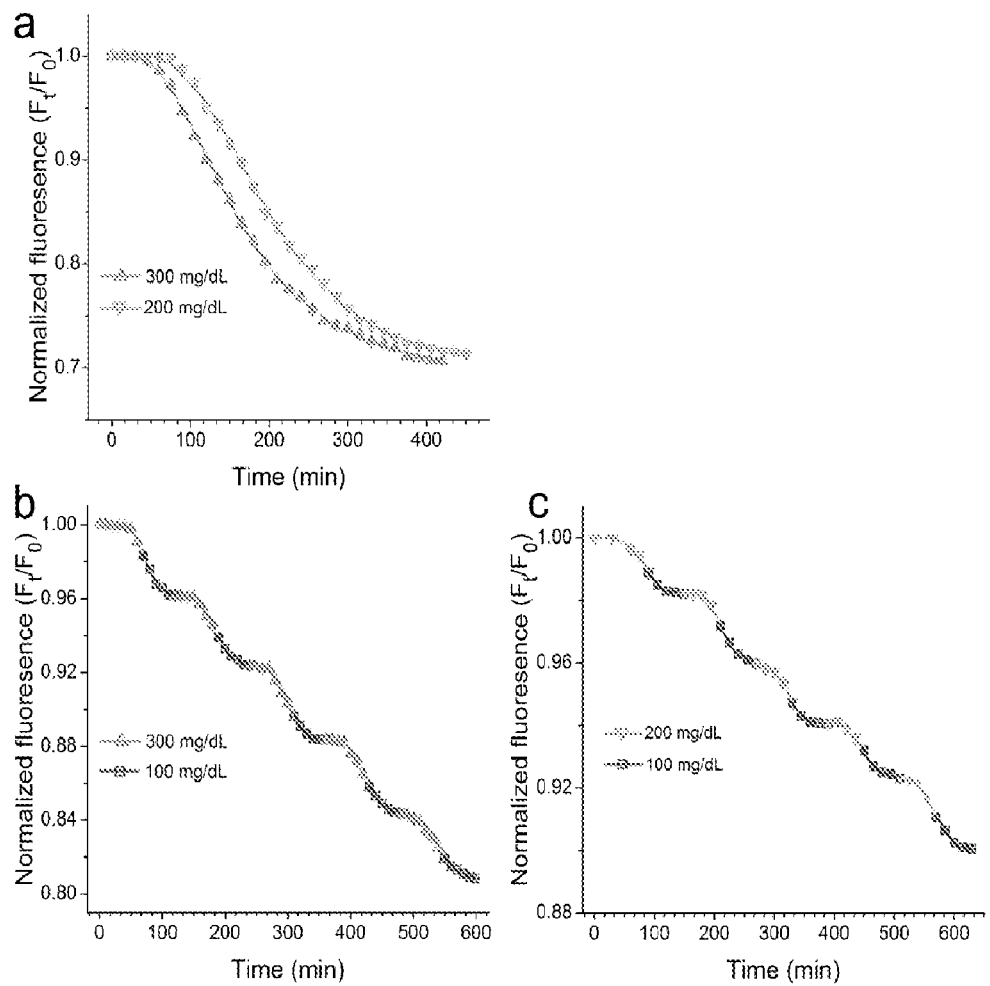

FIG. 19 shows a, FRET assay to study the interactions of peptide-E and peptide-K at modest hyperglycemic concentrations. $F_0$ and $F_t$ represent the fluorescence intensity measured before and at time t after addition into glucose solutions. b and c, Step decrease in fluorescence intensity of peptide-donor by switching the glucose concentrations. Data points represent mean±SD (n=3).

Figure 20:
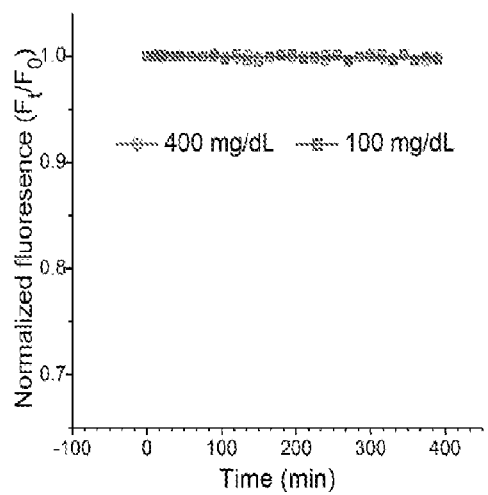

FIG. 20 is a graph depicting a FRET assay to study the interactions of the peptide anchored on OLVs and ISVs surfaces at different glucose concentrations, where the ISVs were modified with non-pH-responsive DNA bridged PEG shield, and peptide-K and peptide-E were modified nitrobenzofuran (peptide-donor) and tetramethylrhodamine (peptide-acceptor), respectively. $F_0$ and $F_t$ represent the fluorescence intensity of peptide-donor measured before and at time t after addition into glucose solutions. The data indicated that by using non-pH-controllable PEG shield, the peptide-K on the ISV surfaces were hindered to interact with the peptide-E on OLV inner surfaces. Data points represent mean±SD (n=3).

Figure 21:
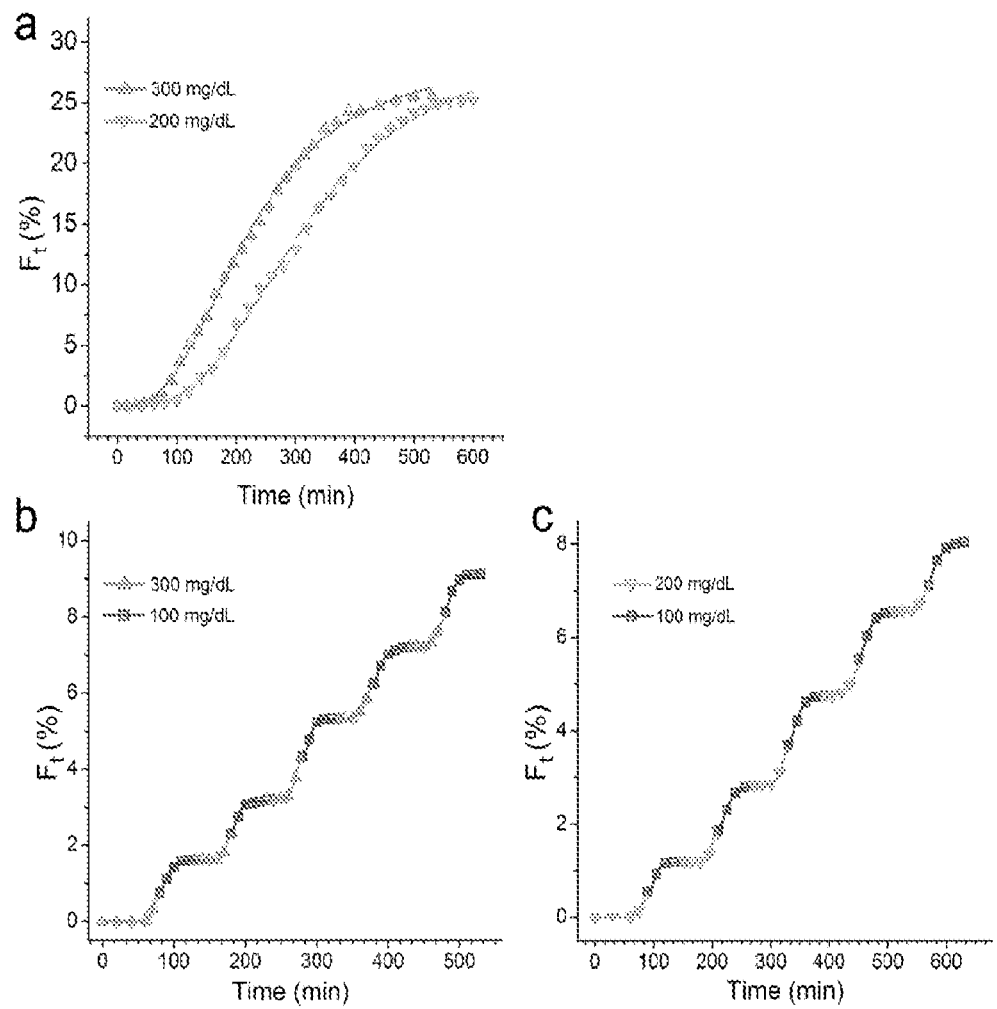

FIG. 21 shows a, Kinetics profiles of lipid mixing between lipid-donor/acceptor-labeled ISV and OLV in 300 mg/dL and 200 mg/dl glucose solutions as indicated by the increase in lipid-donor emission. b and c, Step increase in the fluorescence of lipid-donor after alternatively changing the glucose concentrations. Data points represent mean±SD (n=3).

Figure 22:
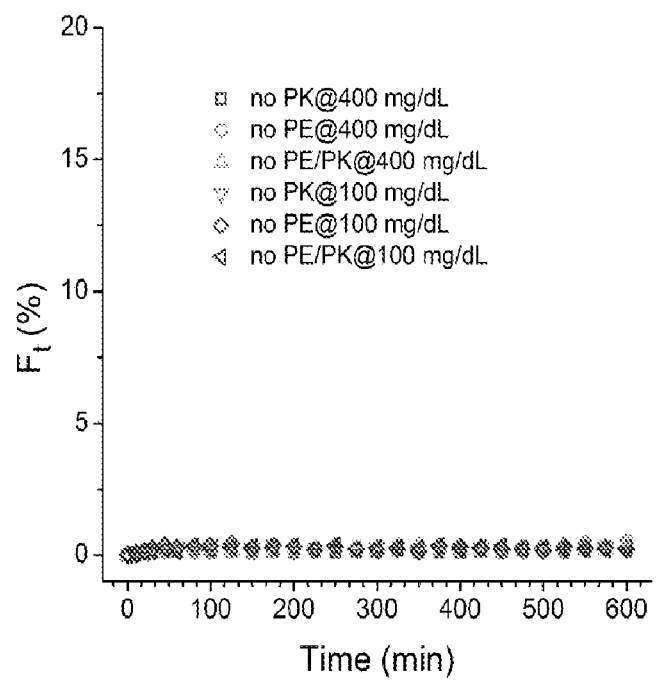

FIG. 22 is a graph depicting lipid mixing between ISV and OLV as indicated by the variation in NBD florescence in control AβCs in which peptide-K (PK), or peptide-E (PE), or peptide-E and peptide-K (PE/PK) were omitted. Lacking the machinery for membrane fusion, no lipid mixing was detected at either high or low glucose concentrations. Data points represent mean±SD (n=3).

Figure 23:
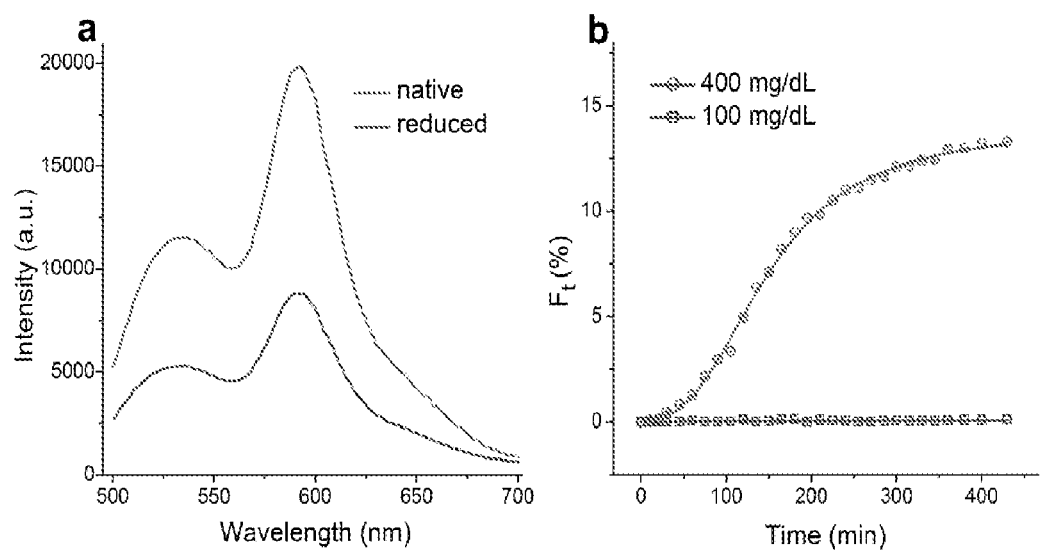

FIG. 23 shows a, Fluorescence spectra of lipid-donor/lipid-acceptor co-labeled ISV before (red line) and after (green line) reduction by sodium dithionate. b, Kinetics profiles showed the mixing of the inner-layer lipids of lipid-donor/lipid-acceptor co-labeled ISV with OLV in 400 mg/dL and 100 mg/dl glucose solutions as indicated by the increase in lipid-donor emission. Data points represent mean±SD (n=3).

Figure 24:
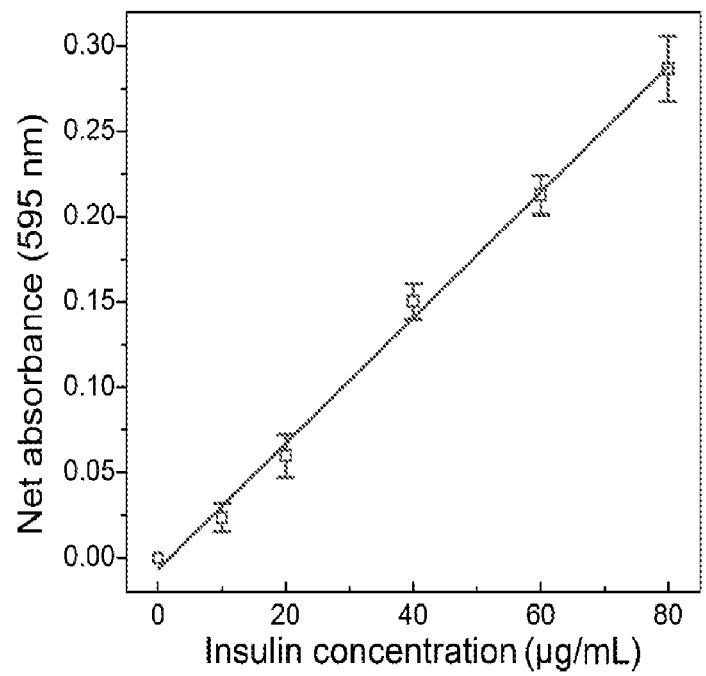

FIG. 24 is a graph depicting an insulin standard curve obtained by Coomassie Plus protein assay. Data points represent mean±SD (n=3).

Figure 25:
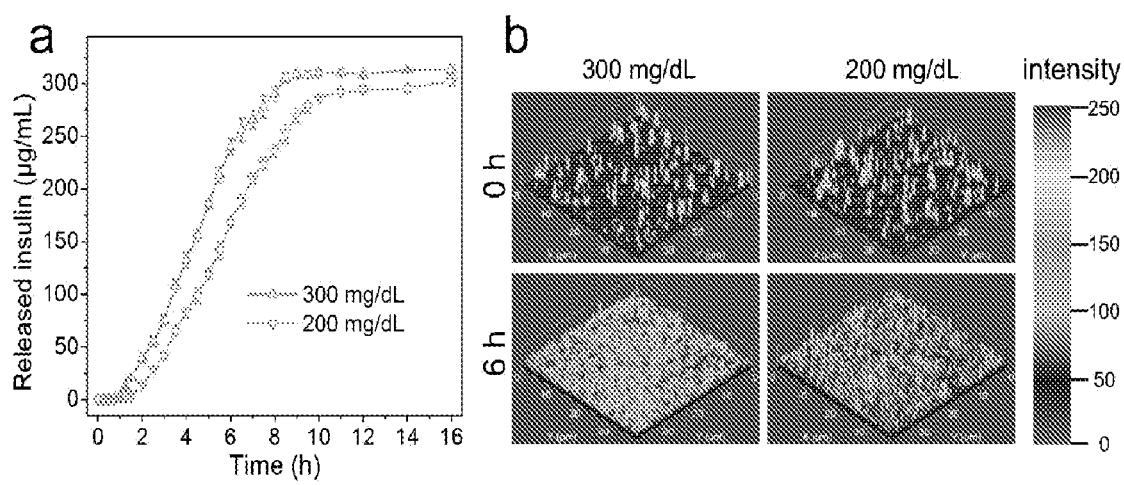

FIG. 25 shows a, In vitro accumulated insulin release from AβCs incubated in solutions with modest hyperglycemic concentrations. Data points represent mean±SD (n=3). b, 2.5D confocal laser microscopy images showed the fluorescence intensity and distribution of fluorescein labeled-insulin from AβCs before and after incubation in solutions containing different concentrations of glucose.

Figure 26:
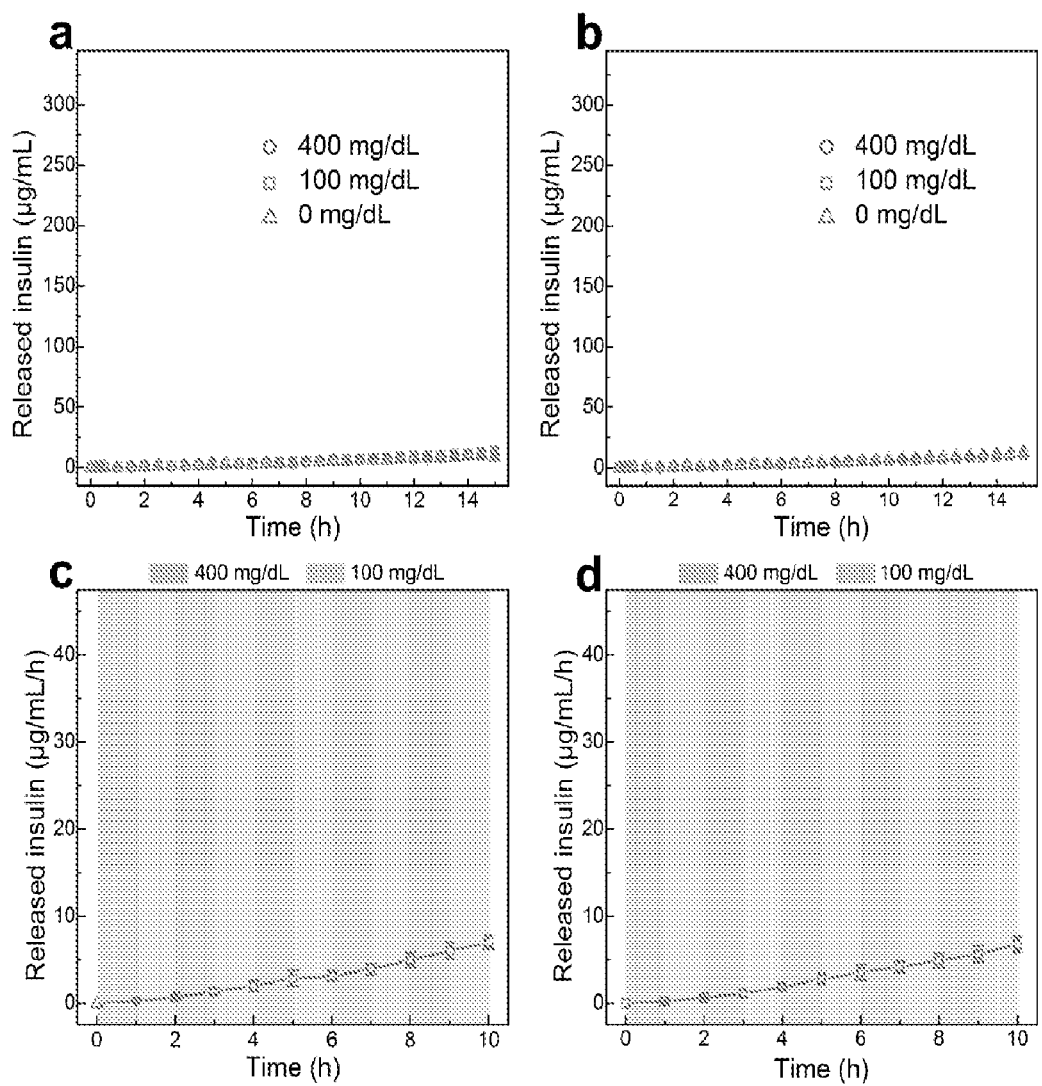

FIG. 26 is a set of graphs depicting in vitro accumulated insulin release from control AβCs (a) lacking glucose sensing machinery (glucose transporter 2, glucose oxidase/catalase, and gramicidin) and (b) with no membrane fusion machinery (peptide-E and peptide-K) at different glucose levels. c and d respectively showed the rate of the pulsatile insulin release profile by the control AβCs used in a and b in response to glucose concentration switch between 400 and 100 mg/dL. Data points represent mean±SD (n=3).

Figure 27:
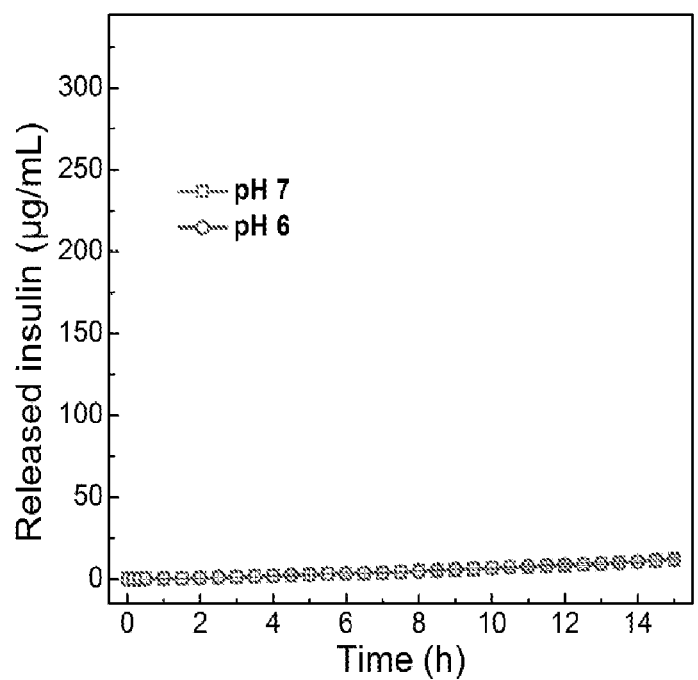

FIG. 27 is a graph depicting in vitro accumulated insulin release from AβCs in mild acidic environment. Data points represent mean±SD (n=3).

Figure 28:
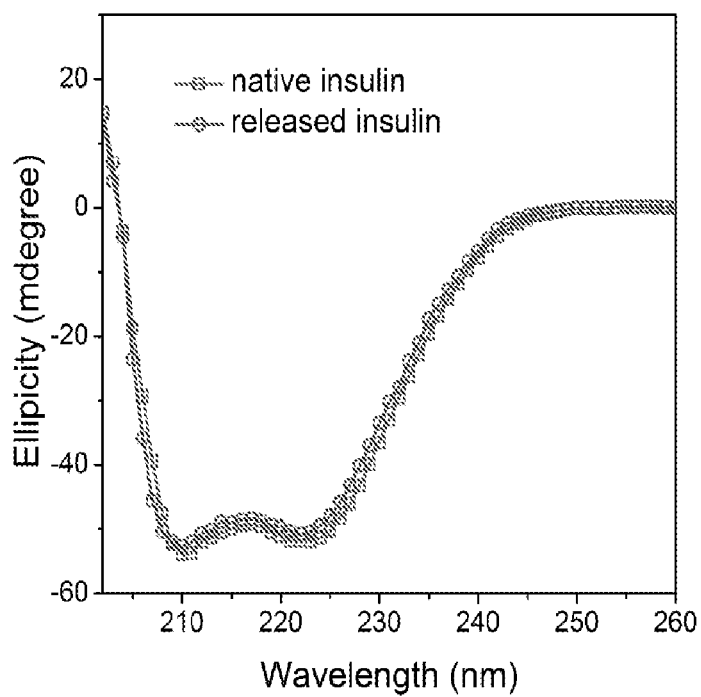

FIG. 28 is a graph depicting the CD spectra of the solutions containing native insulins and released insulins from AβCs incubated with 400 mg/dL glucose. Overall secondary structure of released insulins was maintained to that of native insulins.

Figure 29:
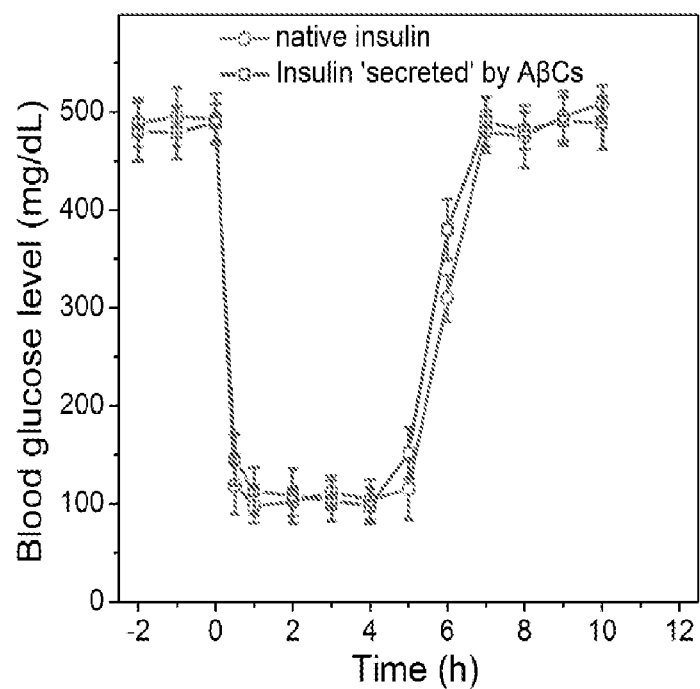

FIG. 29 is a graph comparing the bioactivity of the insulin 'secreted' by AβCs after incubation with 400 mg/dL glucose and that of native insulin. Results showed that the bioactivity of insulin was highly retained during the AβC preparation and release test. Data points represent mean±SD (n=5).

Figure 30:
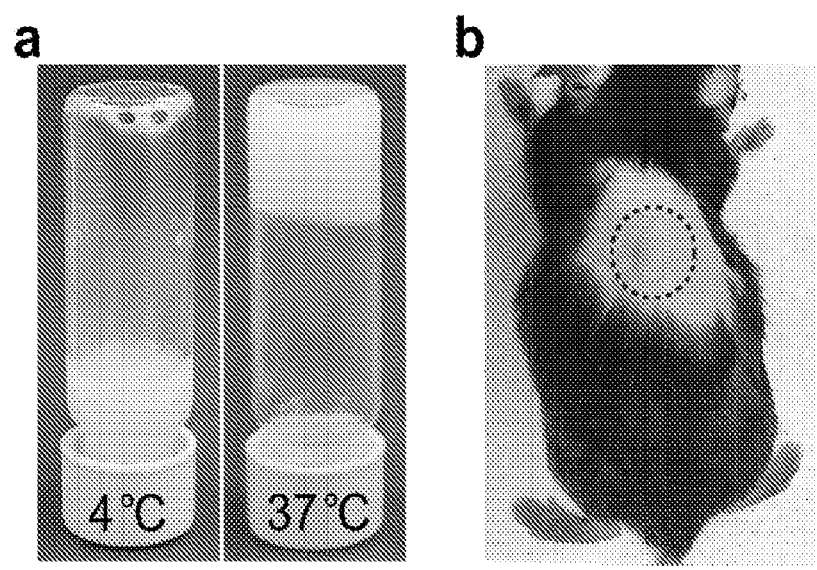

FIG. 30 is a set of photographs depicting AβC integrated thermoresponsive PF127 (40 wt %) solution immediately formed a hydrogel at 37° C. in vitro (a), and 1 min after subcutaneously injection (b). As seen in b, the hydrogel presented as a 'bump' on the dorsum of the mouse.

Figure 31:
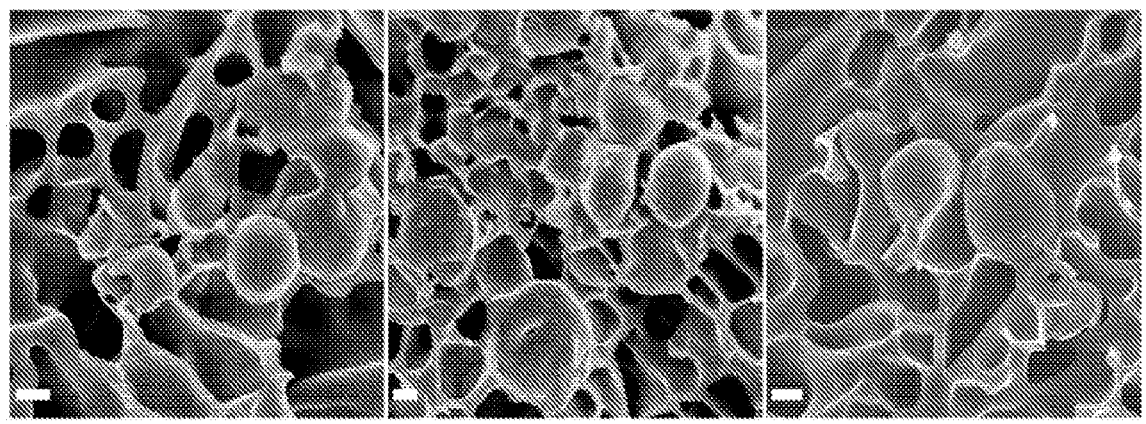

FIG. 31 shows representative cryogenic scanning electron microscopy (cryoSEM) images of the AβC integrated thermoresponsive PF127 solution shown in FIG. 30. Scale bars: 1 μm.

Figure 32:
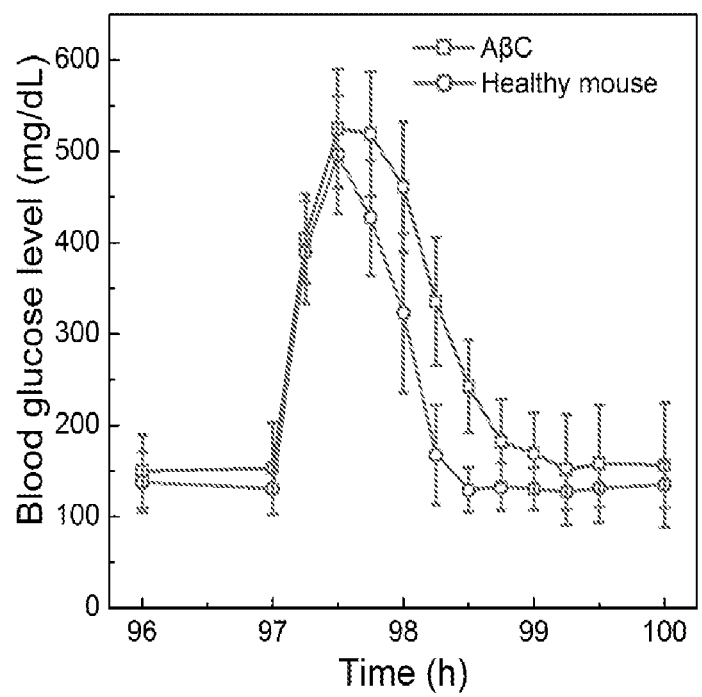

FIG. 32 is a graph depicting in vivo intraperitoneal glucose tolerance test (IPGTT) performed toward diabetic mice on day five following AβC treatment in comparison to the healthy control mice. Data points represent mean±SD (n=5).

Figure 33:
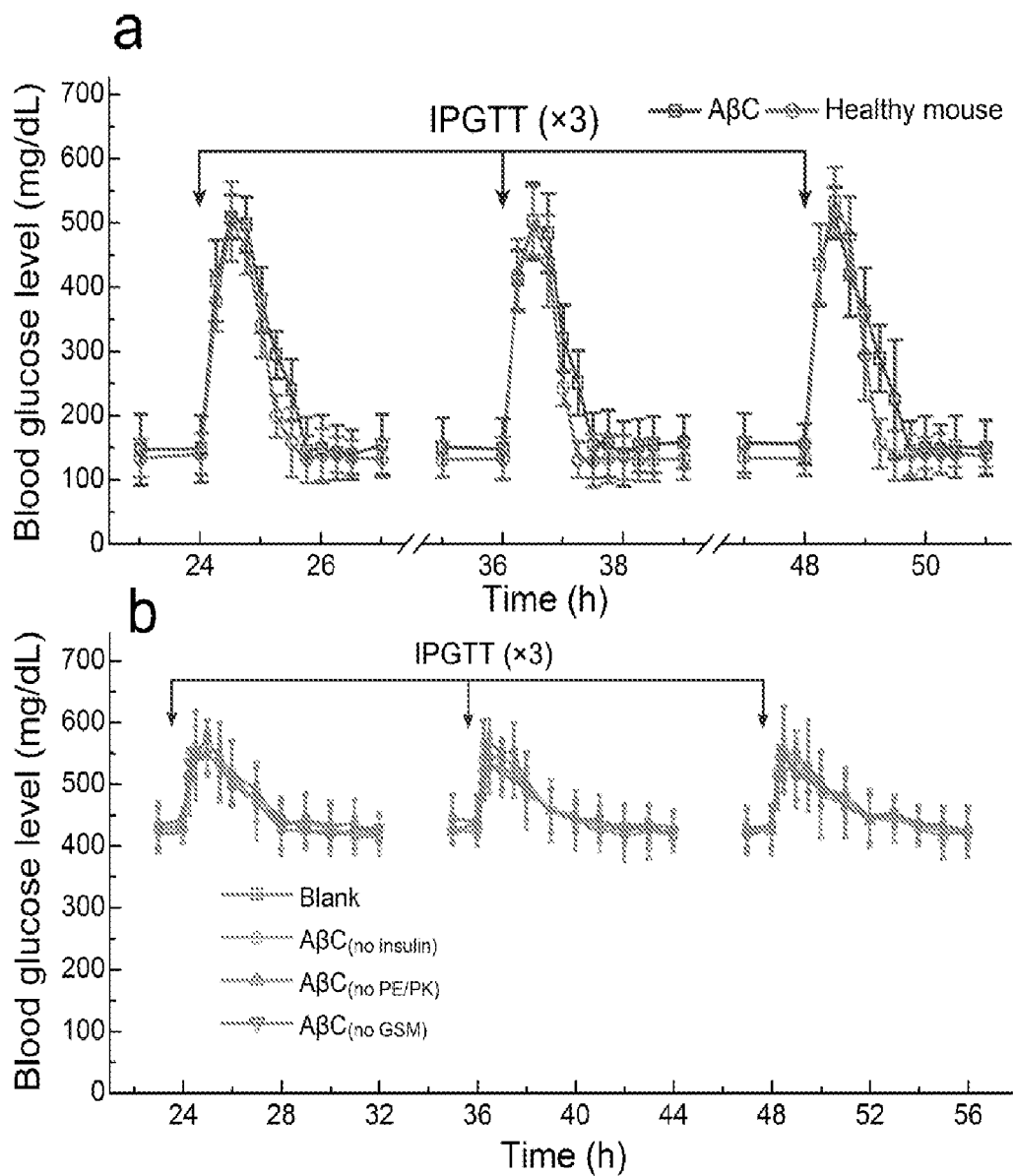

FIG. 33 shows (a) In vivo intraperitoneal glucose tolerance test (IPGTT) performed toward diabetic mice at 24, 36, and 48 h following AβC treatment in comparison to the healthy control mice. Data points represent mean±SD (n=5). (b) IPGTT performed toward diabetic mice at 24, 36, and 48 h following treatment with PBS (Blank) and control AβCs. The remained high blood glucose levels in the control groups as well as the insignificant difference in blood glucose variation between PBS-treated and control AβC-treated groups demonstrated the lack of responsiveness of the control AβCs. Data points represent mean±SD (n=5).

Figure 34:
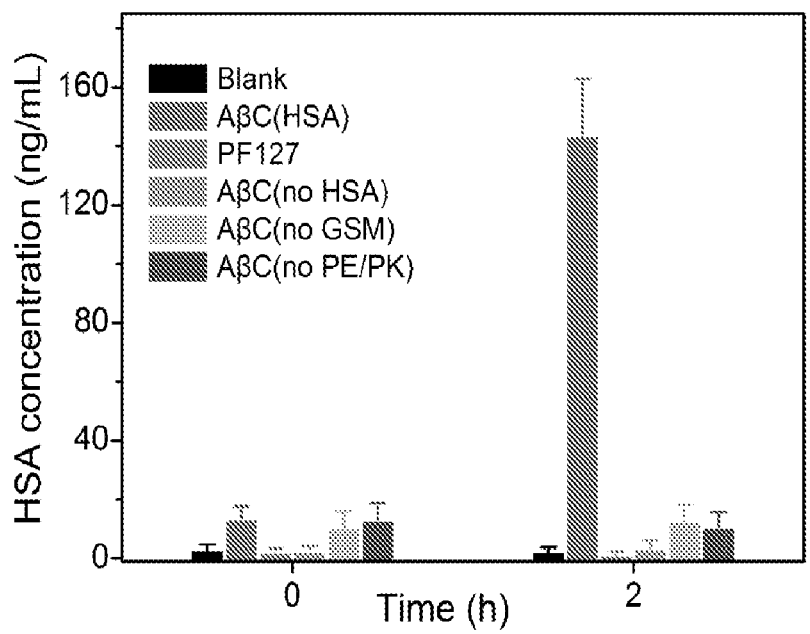

FIG. 34 is a bar chart depicting in vivo intraperitoneal glucose tolerance test (IPGTT) performed towards wild-type mice transplanted with AβCs that were loaded with human serum albumin (HSA) as a reporter protein. The human serum albumin in the serum of each group were measured by ELISA at 2 h after intraperitoneal injection of 50 mg glucose/mouse. Data points represent mean±SD (n=5).

Figure 35:
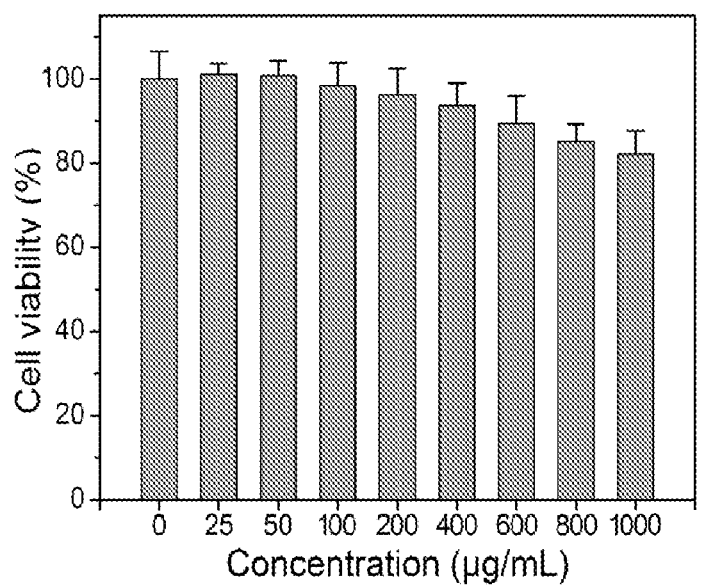

FIG. 35 is a bar chart depicting results of a cytotoxicity assay of insulin-free AβC toward HeLa cells after 24 h incubation. Data points represent mean±SD (n=3).

Figure 36:
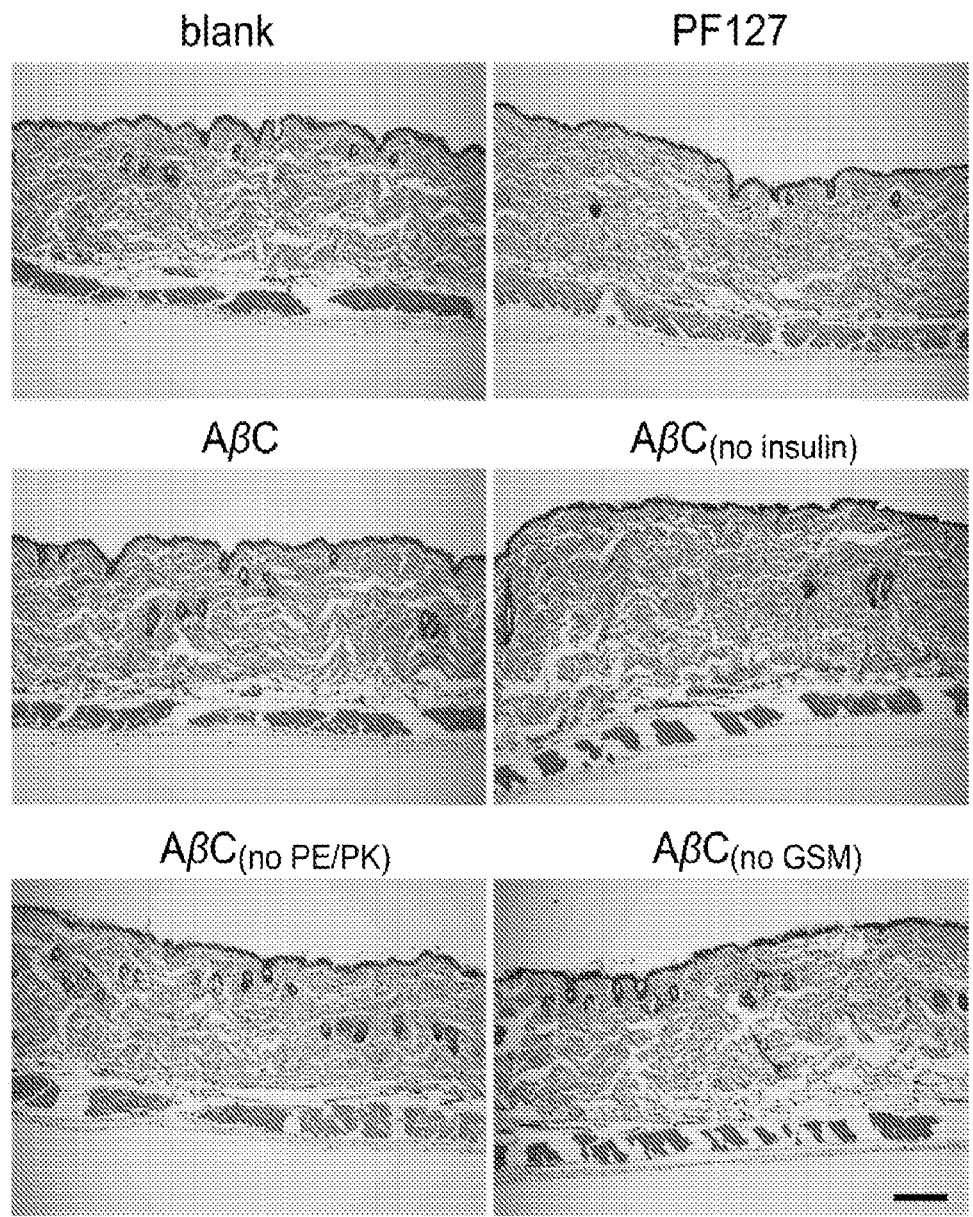

FIG. 36 shows hematoxylin and eosin-stained sections of subcutaneously injected with PBS solution (blank), PF127 thermogel, or 'transplanted' with AβC, AβC$_{(no\ insulin)}$, AβC$_{(no\ PE/PK)}$, or AβC$_{(no\ GSM)}$ after four weeks, respectively. Results showed that all the components were degraded and no noticeable inflammatory region or fibrotic encapsulation was observed, indicating the biocompatibility of the artificial assemblies. Scale bar: 150 μm.

Figure 37:
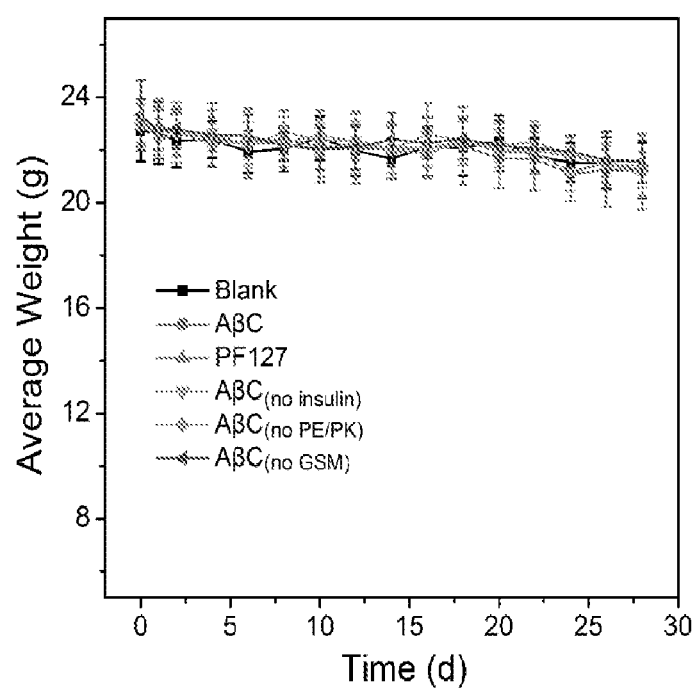

FIG. 37 is a graph depicting the average body weight of the diabetes mice after injection with PBS solution (blank), PF127 thermogel, or 'transplanted' with AβC, AβC$_{(no\ insulin)}$, AβC$_{(no\ PE/PK)}$, or AβC$_{(no\ GSM)}$ for four weeks, respectively. Data points represent mean±SD (n=5).

Figure 38:
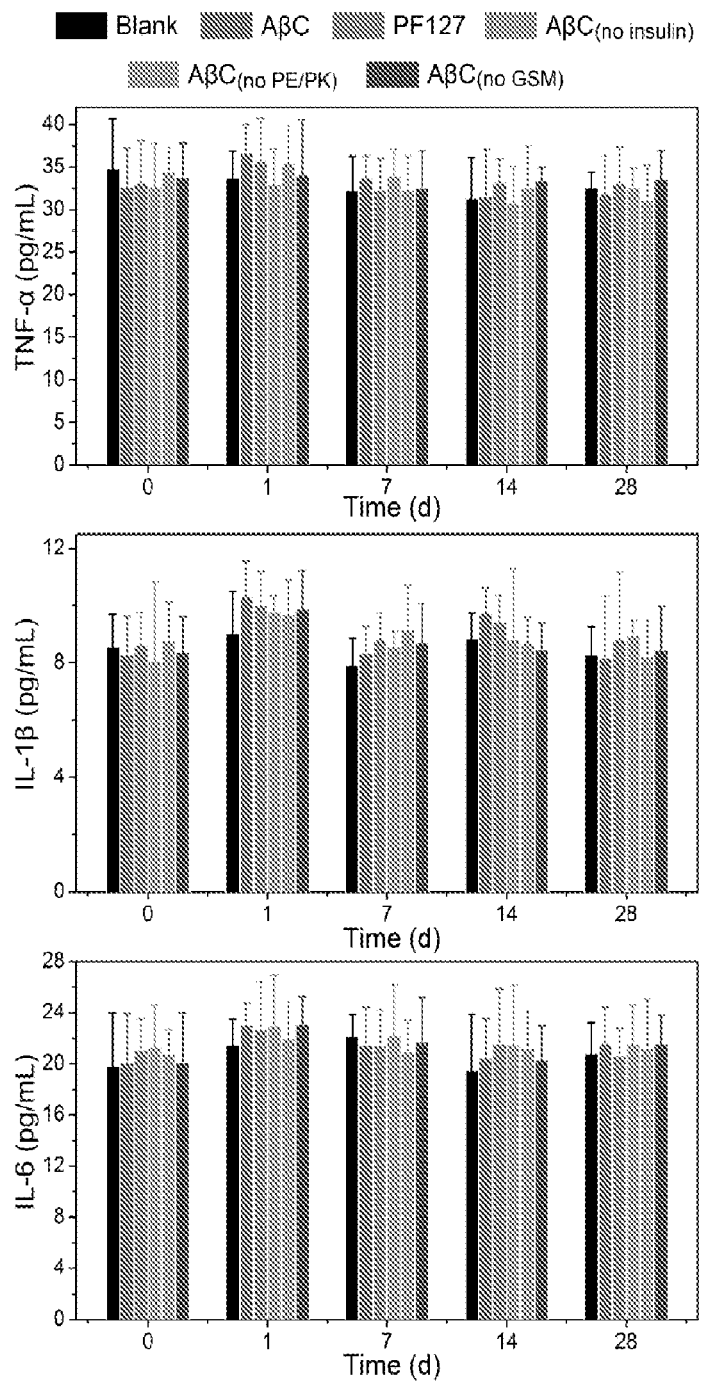

FIG. 38 is a set of bar charts depicting serum levels of TNF-α, IL-1β and IL-6 in diabetes mice after injection with PBS solution (blank), PF127 thermogel, or 'transplanted' with AβC, AβC$_{(no\ insulin)}$, AβC$_{(no\ PE/PK)}$, or AβC$_{(no\ GSM)}$, respectively. Data points represent mean±SD (n=5).

DETAILED DESCRIPTION

Pancreatic β-cells precisely sense blood glucose fluctuations and in turn secret insulin to maintain normoglycemia. Disclosed herein is a novel particle having a sense-and-response system for the delivery of a therapeutic agent (e.g., insulin), which can be useful as an artificial β-cell. This system is the first of its kind to sense glucose levels and readily secrete insulin using a vesicle fusion-mediated behavior. The particle contains a "vesicle-in-vesicle" superstructure that, in some embodiments, is spatially equipped with a pH-altering agent (e.g., a glucose metabolism system) and membrane fusion machinery. For instance, an inner small liposomal vesicle (ISV) can be loaded with insulin to mimic the storage granules inside mature β-cells, while an outer large vesicle (OLV) can mimic a plasma membrane. Metabolism of glucose within the particle can be sensed (e.g., by a glucose-responsive component) and tied to delivery of a therapeutic agent via membrane fusion. Changes in pH within the particle due to glucose metabolism facilitate membrane fusion. The inventors discovered that the particle can effectively distinguish between high and normal glucose levels and respond appropriately with the release of entrapped therapeutic agent. Thus, the particle has the capability to mimic functions of pancreatic β-cells by sensing and distinguishing hyperglycemic and normoglycemic conditions via metabolizing glucose, and responding to hyperglycemic conditions by releasing a therapeutic agent though an exocytosis-like membrane fusion mechanism. At least one of several goals achieved by the particle is delivery of a therapeutic agent (e.g. insulin) in physiologic conditions in which presence of the therapeutic agent would be beneficial (e.g. hyperglycemia), and avoiding the delivery of a therapeutic agent in physiologic conditions in which the presence of the therapeutic agent would provide little or no therapeutic advantage or, in some instances, even cause deleterious effects (e.g. normoglycemia or hypoglycemia).

As depicted in an example embodiment in FIG. 1A, glucose can be taken up by an anchored glucose transporter 2 and subsequently oxidized into gluconic acid by glucose oxidase. The released protons can rapidly decrease the pH in the system. The net pH variation can be balanced by efflux through proton channels-gramicidin A inserted in the OLV membrane, which facilitates more significant variation in the internal pH levels in hyperglycemic conditions. Subsequently, the low pH associated with high glucose concentrations can trigger dehybridization of the PEG5000-conjugated cytosine-rich DNA (PEG-CDNA) and the cholesterol-ended guanine-rich DNA (GDNA-CH) anchored on the ISV, which sterically deshields peptide-K, making it available to form coiled coils with peptide-E (Marsden, H. et al., Chem. Soc. Rev. 40, 1572-1585 (2011); Lygina, A. et al., Angew. Chem. Int. Ed. 50, 8597-8601 (2011); Robson Marsden, H., et al., Chem. Int. Ed. 48, 2330-2333 (2009); Meyenberg, K., et al., Chem. Commun. 47, 9405-9407 (2011); Tomatsu, I. et al., J. Mater. Chem. 21, 18927-18933 (2011); Kong, L., et al., Angew. Chem. Int. Ed. 55, 1396-1400 (2016); Gong, Y., et al., J. Am. Chem. Soc. 130, 6196-6205 (2008); Chan, Y. et al., Proc. Natl Acad. Sci. USA 106, 979-984 (2009); Steinmetz, M. et al., Proc. Natl Acad. Sci. USA 104, 7062-7067 (2007)) on the inner surface of OLV. Zippering up of the two peptides pulls the membranes of ISV and OLV tightly together and forces fusion, upon which insulin is "exocytosed". When glucose concentration declines to a normoglycemic range, glucose uptake can decrease and the inner pH level can increase, which can facilitate the ISVs to re-anchor with PEG-CDNA and subsequently inhibit the fusion event. In this biomimetic manner, the AβC can effectively respond to hyperglycemia and resume the basic low level insulin release under resting conditions.

Reference will now be made in detail to the embodiments of the invention, examples of which are illustrated in the drawings and the examples. The present disclosure may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purposes. A control can be "positive" or "negative."

"Controlled release" or "sustained release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

"Peptide," "protein," and "polypeptide" are used interchangeably to refer to a natural or synthetic molecule comprising two or more amino acids linked by the carboxyl group of one amino acid to the alpha amino group of another.

"Pharmaceutically acceptable" component can refer to a component that is not biologically or otherwise undesirable, e.g., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, preservatives (e.g., Thimerosal, benzyl alcohol, parabens), binders, fillers, disintegrants, sorbents, solvents, pH modifying agents, antioxidants, antiinfective agents, suspending agents, wetting agents, viscosity modifiers, tonicity agents, and other components and combinations thereof or other material well known in the art for use in pharmaceutical formulations and as described further herein. Suitable pharmaceutically acceptable excipients are preferably selected from materials which are generally recognized as safe (GRAS), and may be administered to an individual without causing undesirable biological side effects or unwanted interactions. Suitable excipients and their formulations are described in Remington's Pharmaceutical Sciences, 16th ed. 1980, Mack Publishing Co.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Primer" or "DNA primer" is a short polynucleotide, generally with a free 3'—OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in "PCR: A PRACTICAL APPROACH" (M. MacPherson et al., IRL Press at Oxford University Press (1991)). All processes of producing replicate copies of a polynucleotide, such as PCR or gene cloning, are collectively referred to herein as "replication." A primer can also be used as a probe in hybridization reactions, such as Southern or Northern blot analyses. Sambrook et al., supra.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., Type 1 diabetes). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, palliatively or remedially. Prophylactic treatments are administered to a subject prior to onset (e.g., before obvious signs of diabetes), during early onset (e.g., upon initial signs and symptoms of diabetes), or after an established development of diabetes. Prophylactic administration can occur for day(s) to years prior to the manifestation of symptoms of an infection.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value" 10" is disclosed, then "about 10" is also disclosed.

Publications cited herein are hereby specifically incorporated by reference in their entireties and at least for the material for which they are cited.

Particles

In one aspect, disclosed herein is a particle comprising: an inner liposomal vesicle (ILV) encapsulating a therapeutic agent; an outer liposomal vesicle (OLV) encapsulating the ILV; a membrane fusion-promoting agent; and a pH-altering agent.

In some instances, the ILV can be referred to as an insulin-loaded fusogenic small liposomal vesicle, an inner small liposomal vesicle, or ISV. In some instances, the OLV can be referred to as an outer large vesicle, or an outer large liposomal vesicle.

The particle contains a vesicle-in-vesicle superstructure in which the ILV is encapsulated within the OLV. Because the particle contains a sense-and-response system and a vesicle-in-vesicle superstructure, the particle mimics a biological cell, particularly a pancreatic β-cell. As such, the particle is sometimes referred to herein as an artificial β-cell (AβC).

Typically, ILVs can first be formed, then added to lipid sheets that are induced to close around an ILV to form the vesicle-in-vesicle superstructure. In some embodiments, the OLV encapsulates one or more ILVs. In some embodiments, the OLV encapsulates a plurality of ILVs. Optionally, the OLV encapsulates a mixture of ILVs. Optionally, the mixture of ILVs comprises a first ILV encapsulating a first therapeutic agent and a second ILV encapsulating a second therapeutic agent.

Optionally, the OLV is a vesicle comprising lipids. Optionally, the OLV is a liposomal vesicle comprising a lipid membrane such as a lipid-bilayer membrane. Lipids used to form the bilayer membrane of the OLV can be any lipids suitable for liposome formation. The lipids can be biological lipids, for instance lipids extracted from or extractable from a biological cell. Optionally, the lipids are phospholipids (e.g., phosphatidylcholine, phosphatidylethanolamine, etc.). Mixtures or combinations of lipids can be used to form liposomal lipid bilayer membranes.

The OLV can have a range of sizes, but must be larger than the ILV to encapsulate the ILV. In some embodiments, the OLV can have an average diameter of greater than 100 nm, 250 nm, 500 nm, 750 nm, 1 µm, 1.5 µm, 2.0 µm, 2.5 µm, 3.0 µm, 3.5 µm, 4.0 µm, 4.5 µm, or greater than 5.0 µm. In some embodiments, the OLV can have an average diameter of less than 10 µm, 9 µm, 8 µm, 7 µm, 6 µm, 5 µm, 4 µm, 3 µm, 2 µm, or less than 1 µm. It is understood that the OLV can have an average diameter ranging from any of the minimum values to any of the maximum values described above. For example, the OLV can have an average diameter ranging from 100 nm to 10 µm, or from 1 µm to 5 µm, etc.

Optionally, the ILV is a vesicle comprising lipids. Optionally, the ILV is a liposomal vesicle comprising a lipid membrane such as a lipid-bilayer membrane. Lipids used to form the bilayer membrane of the ILV can be any lipids suitable for liposome formation. The lipids can be biological lipids, for instance lipids extracted from or extractable from a biological cell. Optionally, the lipids are phospholipids (e.g., phosphatidylcholine, phosphatidylethanolamine, etc.) or derivatives of phospholipids (e.g., egg phosphatidylcholine, dioleoyl-glycero-phosphoethanolamine, palmitoylphosphatidylcholine, etc.). Mixtures or combinations of lipids can be used to form liposomal lipid bilayer membranes. The ILV can contain the same or different lipids compared to the OLV. Typically, selected ILV lipids can be fusogenic with the OLV; in other words, the selected ILV lipids can be capable of forming a lipid bilayer membrane that can fuse with the lipid bilayer membrane of the OLV.

The ILV can be a range of sizes, but must be smaller than the OLV to be encapsulated within the OLV. In some embodiments, the ILV can have an average diameter of greater than 1 nm, 10 nm, 20 nm, 30 nm, 40 nm, 50 nm, 60 nm, 70 nm, 80 nm, 90 nm, 100 nm, 150 nm, 200 nm, 300 nm, 400 nm, 500 nm, 1 µm, 1.5 µm, 2.0 µm, 2.5 µm, or greater than 3.0 µm. In some embodiments, the ILV can have an average diameter of less than 5 µm, 4 µm, 3 µm, 2 µm, 1 µm, 750 nm, 500 nm, 400 nm, 300 nm, 250 nm, 200 nm, 150 nm, 100 nm, 90 nm, 80 nm, 70 nm, 60 nm, 50 nm, 40 nm, 30 nm, 20 nm, or less than 10 nm. It is understood that the ILV can have an average diameter ranging from any of the minimum values to any of the maximum values described above. For example, the ILV can have an average diameter ranging from 1 nm to 5 µm, or from 10 nm to 1 µm, or from 10 nm to 100 nm, etc.

The particle comprises an ILV encapsulating a therapeutic agent. The therapeutic agent can be any agent capable of being encapsulated within, and subsequently released from, an ILV to impart a therapeutic effect. The therapeutic agent can be encapsulated within the aqueous-filled interior region of the ILV. For instance, the therapeutic agent can be a hydrophilic compound or biomolecule. The therapeutic agent can be partially or fully embedded in the lipid bilayer membrane of the ILV. For instance, the therapeutic agent can be a hydrophobic or lipophilic compound. In some embodiments, the therapeutic agent can be attached to the ILV, for instance by a linking molecule such as a polyethylene glycol (PEG) molecule. Optionally, the ILV can encapsulate one or more therapeutic agents.

In some embodiments, the therapeutic agent is an agent which treats glycemic imbalance. In some embodiments, the therapeutic agent is an agent which treats hyperglycemia. In some embodiments, the therapeutic agent is an agent which treats diabetes. In some embodiments, the therapeutic agent can be a peptide, protein, signally molecule (e.g., hormone), small molecule, carbohydrate, nucleic acid molecule, lipid, organic molecule, biologically active inorganic molecule, or combinations thereof. Optionally, the therapeutic agent can comprise insulin or a biologically active compound derived from insulin.

In some embodiments, the therapeutic agent can be used to treat diabetes, such as insulin, alpha-glucosidase inhibitors (e.g., acarbose, miglitol), biguanides (e.g., metformin), dopamine agonists (e.g., bromocriptine), DPP-4 inhibitors (e.g., alogliptin, alogliptin-metformin, alogliptin-pioglitazone, linagliptin, linagliptin-empagliflozin, linagliptin-metformin, saxagliptin, saxagliptin-metformin, sitagliptin, sitagliptin-metformin, sitagliptin and simvastatin), glucagon-like peptides/incretin mimetics (e.g., albiglutide, dulaglutide, exenatide, exenatide extended-release, liraglutide, semaglutide), meglitinides (e.g., nateglinide, repaglinide, repaglinide-metformin), sodium glucose transporter (SGLT) 2 inhibitors (e.g., dapagliflozin, dapagliflozin-metformin, canagliflozin, canagliflozin-metformin, empagliflozin, empagliflozin-linagliptin, empagliflozin-metformin, ertugliflozin), sulfonylureas (e.g., glimepiride, glimepiride-pioglitazone, glimepiride-rosiglitazone, gliclazide, glipizide, glipizide-metformin, glyburide, glyburide-metformin, chlorpropamide, tolazamide, tolbutamide), thiazolidinediones (e.g., rosiglitazone, rosiglitazone-glimepiride, rosiglitazone-metformin, pioglitazone, pioglitazone-aloglitptin, pioglitazone-glimepiride, pioglitazone-metformin), and combinations thereof.

Optionally, the ILV can encapsulate an additional agent or, alternatively or in addition to, the OLV can encapsulate a first ILV encapsulating a therapeutic agent and a second ILV encapsulating an additional agent. Optionally, the additional agent can be a therapeutic, prophylactic, or diagnostic agent.

The herein disclosed particle comprises a membrane fusion-promoting agent. The membrane fusion-promoting agent can promote fusion between the ILV and the OLV or, in some embodiments, between an ILV lipid bilayer membrane and an OLV lipid bilayer membrane. Optionally, the membrane fusion-promoting agent is attached to the surface of a lipid bilayer membrane. Such attachment can be non-covalent (e.g., by hydrophobic insertion) or covalent (e.g., by covalent linkage directly to a lipid or to a linking molecule). When accessible, the membrane fusion-promoting agent can be specifically bound and subsequently promote membrane fusion. Membrane fusion activity can be inhibited by, for example, blocking accessibility of the membrane fusion-promoting agent or by altering the conformation of the membrane fusion-promoting agent. In some embodiments, the membrane fusion-promoting agent can cycle between an accessible state and a blocked state.

In some embodiments, the membrane fusion-promoting agent can be specifically bound by dimerizing. For example, a first copy of the membrane fusion-promoting agent can specifically bind a second copy of the membrane fusion-promoting agent. Specific binding of the membrane fusion-promoting agent can facilitate fusion between two or more membranes (e.g. lipid bilayer membranes). Without being limited to a particular mechanism, the specific binding of the membrane fusion-promoting agent can bring two or more membranes to within close proximity, particularly when the membrane fusion-promoting agent is bound to the surface of a membrane to be fused, and facilitate local lipid rearrangements which results in fusing of the membranes. As used herein, the term "specific binding" and grammatical variations thereof refers to the binding of a first component to a second component with an affinity greater than the affinity of the first component for generally any other component in the particle (e.g., background or non-specific binding). In some embodiments, the term "specific binding" refers to the binding of two or more components to form a biological complex having a biological function, wherein the two or more components have an affinity for each other greater than the affinity for non-specific binding components.

Optionally, the membrane fusion-promoting agent comprises a first membrane fusion-promoting agent and a second membrane fusion-promoting agent. Optionally, the first membrane fusion-promoting agent is attached to the ILV, for instance to the outer surface of the ILV, and the second membrane fusion-promoting agent is attached to the OLV, for instance to the inner surface of the OLV. Optionally, the attachment of membrane fusion-promoting agents to lipid vesicles is reversed: the first membrane fusion-promoting agent is attached to the OLV, for instance to the inner surface of the OLV, and the second membrane fusion-promoting agent is attached to the ILV, for instance to the outer surface of the ILV.

The membrane fusion-promoting agent can be any suitable agent which, when specifically bound, facilitates membrane fusion. Thus, the membrane fusion-promoting agent can be any protein, peptide, nucleic acid, lipid, carbohydrate, synthetic polymer, small molecule attached to e.g., a lipid or synthetic polymer (e.g., a polyethylene glycol (PEG) or pegylated-molecule), etc. In some embodiments, the membrane fusion-promoting agent comprises a biological molecule. In some embodiments, the membrane fusion-promoting agent can facilitate membrane fusion by positioning (e.g., by pulling) the OLV and ILV in sufficiently close proximity for membrane fusion to occur.

In some embodiments, the membrane fusion-promoting agent comprises a Soluble NSF Attachment Protein Receptor (SNARE) protein. Optionally, the membrane fusion-promoting agent is selected from Peptide-K, Peptide-E, or combinations thereof. Peptide-K refers to a peptide comprising the amino acid sequence $(KIAALKE)_3$ (SEQ ID NO: 1). Peptide-E refers to a peptide comprising the amino acid sequence $(EIAALEK)_3$ (SEQ ID NO:2). In some embodiments, the membrane fusion-promoting agent comprises a first membrane fusion-promoting agent and a second membrane fusion-promoting agent, in which the first membrane fusion-promoting agent is a first SNARE polypeptide (e.g., Peptide-K) and the second membrane fusion-promoting agent is a second SNARE polypeptide (e.g., Peptide-E). When attached and accessible on the outer surface of an ILV, a first SNARE polypeptide (e.g., Peptide-K) can specifically bind a second SNARE polypeptide (e.g., Peptide-E) that is attached and accessible on the outer surface of an OLV. Specific binding of Peptide-K and Peptide-E can thus result in membrane fusion between the ILV and OLV.

In some embodiments, the first and second membrane fusion-promoting agents can be complementary nucleic acid molecules (e.g., a first single-stranded DNA molecule which binds a complementary second single-stranded DNA molecule). In some embodiments, the first and second membrane fusion-promoting agents can be a combination of molecule types. For example, a DNA-binding protein can specifically bind a double-stranded DNA molecule, or a lipid-binding protein can specifically bind a lipid integrated in a membrane to be fused.

The herein disclosed particle comprises a pH-altering agent. The pH-altering agent can reduce the pH inside the OLV. A particularly preferable pH-altering agent is an agent which alters the pH in response to a stimulus, for example a stimulus presenting information about conditions outside the OLV. For example, the pH-altering agent can alter the pH in response to biomolecule or substrate concentrations in the surrounding medium (e.g., blood-glucose concentrations). In some embodiments, the pH-altering agent can reduce the pH.

In some embodiments, the pH-altering agent comprises a biological molecule. In some embodiments, the pH-altering agent comprises a polypeptide, for instance an enzyme. Optionally, the pH-altering agent comprises a glucose-responsive enzyme. In some embodiments, the pH-altering agent comprises glucose oxidase (GOx). In such an embodiment, GOx metabolizes glucose within the OLV, releasing protons and reducing the pH within the OLV. Thus, as the glucose concentration within the OLV increases, GOx has access to increased amounts of glucose substrate, resulting in concomitant pH reduction.

In some embodiments, the particle can further contain an enzyme for scavenging metabolism-byproducts, for example a peroxide-metabolizing enzyme. For example, GOx-mediated glucose metabolism may result in production of peroxides, particularly hydrogen peroxide. An enzyme can be present within the OLV which can degrade or scavenge hydrogen peroxide byproduct. In some embodiments, the peroxide-metabolizing enzyme can be catalase (CAT). Catalase provides a further benefit to GOx-mediated glucose metabolism in that catalase can regenerate oxygen to facilitate further glucose oxidation.

In some embodiments, the particle can further contain a small molecule transporter. A small molecule transporter can facilitate the exchange of small molecules between the OLV and the exterior medium in which the particle resides. In some embodiments, the small molecule transporter is integrated in the OLV lipid bilayer liposomal membrane. In some embodiments, the small molecule transporter can be a component of a larger membrane-associated transport system (e.g., a lipid-coupled, multi-protein membrane transport system). In some embodiments, the small molecule transporter is a transmembrane transport protein. The small molecule transporter need not be a dedicated transporter; the small molecule transporter can transport an array of substrates. Preferably, the small molecule transporter transports a small molecule of interest to which the particle "senses" and responds to. As an example, high glucose conditions (e.g., hyperglycemic levels in the blood) can be a stimulus to which the particle responds to. As glucose concentrations in the medium increase, the small molecule transporter (e.g., a glucose membrane transporter) can relay this information to within the OLV by transporting glucose to the interior of the OLV. Thus, hyperglycemic conditions can stimulate increased glucose transport, which can increase GOx-mediated glucose metabolism, thereby resulting in reduced pH within the OLV. In some embodiments, the small molecule transporter comprises a glucose transporter (e.g., Glucose Transporter 2 (GLUT2); also known as solute carrier family 2 or SLC2A2).

In some embodiments, the particle can further contain a proton transporter. In some embodiments, the proton transporter is integrated into the OLV lipid bilayer liposomal membrane. In some embodiments, the proton transporter comprises a prokaryotic polypeptide, for instance a pore-forming protein. Preferably, the proton transporter is oriented in the membrane for the export of protons. Rapid import and subsequent metabolism of a substrate (e.g., glucose) that, when metabolized releases protons, can result in a rapid decrease in pH. In some embodiments, it can be advantageous to temper pH fluctuations to, for example, exert greater control over the rapidity of change or the degree of change. In such embodiments, proton export can counter intravesicle proton production and/or release. In some embodiments, the proton transporter can be Gramicidin A, B, or C.

In some embodiments, the particle can further contain a membrane fusion-inhibiting agent. In some aspects, it may be desirable to prevent membrane fusion, for example between the OLV and ILV. Because ILV-OLV fusion results in release of the therapeutic agent encapsulated in the ILV in some embodiments, release of the therapeutic agent can optionally be restricted or controlled by inhibiting ILV-OLV fusion. The membrane fusion-inhibiting agent can be any agent suitable to inhibit ILV-OLV fusion (for example, by inhibiting lipid membrane fusion) including, for example, peptides, proteins, synthetic polymers, nucleic acids, and the like.

One particularly advantageous membrane fusion-inhibiting agent is one which shields access to the membrane fusion-promoting agent, for example by steric blockade. Such a mechanism can prevent the membrane fusion-promoting agent from being specifically bound, thereby inhibiting a key facilitating step for membrane fusion. Thus, in some embodiments, a membrane fusion-promoting agent containing a first SNARE polypeptide (e.g., Peptide-K) can be blocked from specifically binding a second SNARE polypeptide (e.g., Peptide-E) by a larger molecule which shields access to the first SNARE polypeptide, the second SNARE polypeptide, or both. Thus, in some embodiments, the membrane fusion-inhibiting agent can be attached to the ILV, the OLV, or both.

In some embodiments, the membrane fusion-inhibiting agent can be membrane embedded or attached to lipids of a membrane. In some embodiments, the membrane fusion-inhibiting agent contains a molecule larger than the membrane fusion-promoting agent and thus capable of shielding the membrane fusion-promoting agent. Optionally, membrane fusion-inhibiting agent contains a polyethylene glycol (PEG) molecule. The PEG can be any biocompatible PEG have a sufficiently large size to inhibit specific binding of the membrane fusion-promoting agent. In some embodiments, the PEG has a molecular weight of at least 0.1, 0.5, 1, 2, 3, 4, 5, 6, 7, 8, 9, or 10 kDa. In some embodiments, the PEG can be conjugated with other molecules (e.g., a nucleic acid, lipid, carbohydrate, small molecule, peptide, protein, and the like).

In some embodiments, the membrane fusion-inhibiting agent can also be, for example, a soluble mediator which blocks specific binding of the membrane fusion-promoting agent. As an example, the membrane fusion-promoting agent can be a nucleic acid and the membrane fusion-inhibiting agent can be a soluble DNA-binding protein.

In some embodiments, the membrane fusion-inhibiting agent can be responsive to the stimulus the particle can "sense." Thus, the membrane fusion-inhibiting agent can be blocked from inhibiting membrane fusion under certain conditions. For example, a particle which "senses" high glucose levels in the surrounding medium (e.g., hyperglycemic blood levels) by transporting and metabolizing glucose, thereby reducing the pH within the OLV, can further block the activity of the membrane fusion-inhibiting agent under hyperglycemic conditions. Because high glucose levels in the medium result in pH reduction within the OLV, the membrane fusion-inhibiting agent can be a pH-responsive agent. For example, the membrane fusion-inhibiting agent can be degraded, denatured, sequestered, or otherwise inactivated at low pH. In some embodiments, the membrane fusion-inhibiting agent can be an acid-degradable polyethylene glycol (PEG) molecule. In such embodiments, reduction in pH results in degraded PEG molecules, thereby releasing the steric blockade of the membrane fusion-promoting agent and facilitating subsequent ILV-OLV membrane fusion. A pH-responsive agent (e.g., an acid-degradable PEG) can be responsive at a pH of 7.3 or less, 7.2 or less, 7.1 or less, 7.0 or less, 6.9 or less, 6.8 or less, 6.7 or less, 6.6 or less, 6.4 or less, 6.3 or less, 6.2 or less, 6.1 or less, 6.0 or less, 5.9 or less, 5.8 or less, 5.7 or less, 5.6 or less, 5.5 or less, 5.4 or less, 5.3 or less, 5.2 or less, 5.1 or less, 5.0 or less, 4.9 or less, 4.8 or less, 4.7 or less, 4.6 or less, 4.5 or less, 4.4 or less, 4.3 or less, 4.4 or less, 4.3 or less, 4.2 or less, 4.1 or less, or 4.0 or less.

Optionally, the particle can be formulated in a medicament. The particle can be formulated in any suitable medicament including, for example, but not limited to, an injectable solution, an intravenous drip, a hydrogel, and the like. The medicament can comprise a pharmaceutically acceptable excipient. In some embodiments, the medicament can further comprise an additional diagnostic or therapeutic agent.

Methods

Disclosed herein is a method of delivering a therapeutic agent. The method can include delivering a therapeutic agent to a subject. The method can include providing a particle comprising an inner liposomal vesicle (ILV) encapsulating a therapeutic agent, an outer liposomal vesicle (OLV) encapsulating the ILV, a membrane fusion-promoting agent, and a pH-altering agent. The method can further include triggering ILV and OLV fusion. The method can further include releasing the therapeutic agent outside of the OLV.

The particle can be any particle disclosed herein.

In some embodiments, the triggering step can be in response to a stimulus (e.g., solute concentration in the surrounding medium). In some embodiments, the triggering step can be preceded by a chemical or enzymatic reaction, for instance enzymatic release of protons. In some embodiments, the triggering step can be in response to an altered pH (e.g., a reduced pH) within the OLV.

In some embodiments comprising a small molecule transporter, the method can include transporting a small molecule (e.g., glucose). In such embodiments, the transporting step can include transporting a small molecule substrate into the OLV via the small molecule transporter. In some embodiments, the triggering step can be coupled to the transporting step. For instance, the triggering step can proceed only after the transporting step proceeds.

In some embodiments, the method can include sensing a small molecule. The sensing step can be any form of molecular interaction. For example and without limitation, the sensing step may be performed by binding, degrading, cleaving, sequestering, conjugating, activating, metabolizing, etc. the small molecule. As an example, glucose may be degraded or metabolized by an enzyme. In some aspects, the sensing step is performed by the pH-altering agent. In some aspects, the sensing step comprises degrading the small molecule by the pH-altering agent.

In some aspects, the sensing step provides a signal to which the particle responds. In some embodiments, the sensing step reduces the pH in the OLV. The pH can optionally be reduced below the pH of the surrounding medium. In some embodiments, the pH can be reduced to 7.3 or less, 7.2 or less, 7.1 or less, 7.0 or less, 6.9 or less, 6.8 or less, 6.7 or less, 6.6 or less, 6.4 or less, 6.3 or less, 6.2 or less, 6.1 or less, 6.0 or less, 5.9 or less, 5.8 or less, 5.7 or less, 5.6 or less, 5.5 or less, 5.4 or less, 5.3 or less, 5.2 or less, 5.1 or less, 5.0 or less, 4.9 or less, 4.8 or less, 4.7 or less, 4.6 or less, 4.5 or less, 4.4 or less, 4.3 or less, 4.4 or less, 4.3 or less, 4.2 or less, 4.1 or less, or 4.0 or less.

In some embodiments comprising a particle comprising a proton transporter, the method can further comprise regulating pH within the OLV. pH regulation can occur in part via export of protons by the proton transporter. In some embodiments, the pH can be regulated by a proton-sequestering molecule.

In some embodiments comprising a particle comprising a membrane fusion-inhibiting agent, the method can further comprise inhibiting membrane fusion. Membrane fusion can be inhibited under any general condition or under one or more specific conditions. In embodiments comprising an inhibiting step, the triggering step can be blocked from initiating, continuing, or accelerating. Thus, the inhibiting step can temporarily stall progression of the method until the inhibiting step terminates. The inhibiting step can proceed for any amount of time (seconds, minutes, hours, days, weeks, months, etc.). The inhibiting step can fully or partially inhibit the triggering step.

In embodiments comprising an inhibiting step, the method may further comprise a deshielding step. Thus, in some aspects, the method can comprise deshielding the membrane fusion-promoting agent. The membrane fusion-inhibiting agent can inhibit the membrane fusion-promoting agent in any number of ways which blocks promotion of membrane fusion activity. Thus, "deshielding" is intended to refer to any removal, negation, reduction, etc. of the inhibiting activity of the membrane fusion-inhibiting agent on the membrane fusion-promoting agent. For example and without limitation, deshielding can refer to degrading, denaturing, sequestering, or otherwise inactivating the membrane fusion-inhibiting agent which results in the ability of the membrane fusion-promoting agent to be specifically bound. As an example, the method can comprise deshielding the membrane fusion-promoting agent by acid-degradation of the membrane fusion-inhibiting agent in response to decreased pH within the OLV.

In some embodiments, the inhibiting and deshielding steps can be repeated one or more times, two or more times, three or more times, or four or more times. In some embodiments, the inhibiting and deshielding steps can be cyclical. In some embodiments, repetition of the inhibiting and deshielding steps depends on the sensing step. As an example, the sensing step may reduce the pH in the OLV when the medium contains high levels of glucose, thereby initiating the deshielding step. When the glucose levels in the medium become reduced, the sensing step can cease reducing the pH in the OLV, and a net increase in pH within the OLV can occur. In such instances, the deshielding step can cease, and the inhibiting step can initiate. The number of times the inhibiting and deshielding steps can be repeated is limited by the number of ILVs in the OLV which successfully proceed through to the releasing step. Once an ILV fuses with the OLV and releases encapsulated therapeutic agent, that ILV is no longer available for future releasing steps.

The termination of the deshielding step and initiation of the inhibiting step can occur by any method which restores the inhibiting activity of the membrane fusion-inhibiting agent. For example, protonation and deprotonation can, in some embodiments, regulate the inhibiting activity of the membrane fusion-inhibiting agent. In some embodiments, the membrane fusion-inhibiting agent can be cleaved or degraded in response to reduced pH. In some embodiments, the membrane fusion-inhibiting agent can be reconstituted in response to increased pH, thereby restoring the inhibiting activity of the membrane fusion-inhibiting agent.

The method includes a triggering step comprising triggering ILV and OLV fusion. In some embodiments, the triggering step b) results from the sensing step. The triggering step can include any molecular "trigger" suitable to trigger ILV and OLV fusion. In some embodiments, the sensing step results in decreasing pH, wherein decreasing pH triggers membrane fusion activity. More specifically, in some embodiments, the sensing step results in decreasing pH, wherein decreasing pH results in deshielding the membrane fusion-promoting agent, wherein deshielding results in specific binding of the membrane fusion-promoting agent. In some embodiments, the triggering step can be facilitated by specific binding of the membrane fusion-promoting agent. In some embodiments, the triggering step b) results in fusion of the ILV lipid bilayer liposomal membrane and the OLV lipid bilayer liposomal membrane.

The method includes releasing the therapeutic agent outside of the OLV. Fusion of the ILV with the OLV results in an "exocytosis-like" phenomenon in which encapsulated therapeutic agent is released to the surrounding medium outside the OLV. In some aspects, at least a portion of the therapeutic agent is released. In some aspects, all of the therapeutic agent in an ILV is released. In some aspects, two or more ILVs fuse with the OLV, wherein each ILV releases encapsulated therapeutic agent. Therapeutic agent release by multiple ILVs can occur concurrently, sequentially, or over a relatively long period of time. In embodiments which include two or more repetitions of inhibiting and deshielding steps, two or more releasing steps can also proceed. For example, the method may include a first inhibiting step, then a first deshielding step, then a first releasing step, then a second inhibiting step, then a second deshielding step, then a second releasing step, and so forth.

In some aspects, the releasing step c) is facilitated in hyperglycemic conditions by, for example, inclusion of a deshielding step. In some aspects, the releasing step c) is inhibited in normoglycemic or hypoglycemic conditions by, for example, inclusion of an inhibiting step.

The method includes delivery of an agent in a subject. The subject can be any mammalian subject, for example a human, dog, cow, horse, mouse, rabbit, etc. In some embodiments, the subject comprises a small molecule which can be sensed and responded to by the particle. In some embodiments, the subject has a disease or condition. In some embodiments, the subject has hyperglycemia. In some embodiments, the subject has diabetes.

In another aspect, provided herein is a method for treating a disease in a subject. In some aspects, the subject is in need of treating the disease. In some aspects, the method includes administering to a subject a particle comprising an inner liposomal vesicle (ILV) encapsulating a therapeutic agent, an outer liposomal vesicle (OLV) encapsulating the ILV, a membrane fusion-promoting agent, and a pH-altering agent.

The particle can be any particle disclosed herein.

In some embodiments, the administering step can include any method of introducing the particle into the subject appropriate for the particle formulation. The administering step can include at least one, two, three, four, five, six, seven, eight, nine, or at least ten dosages. The administering step can be performed before the subject exhibits disease symptoms (e.g., prophylactically), or during or after disease symptoms occur. The administering step can be performed prior to, concurrent with, or subsequent to administration of other agents to the subject. In some embodiments, the administering step is performed without administration of immunosuppressive agents. In some embodiments, the particle is administered in a hydrogel.

In some embodiments, a subsequent administration is provided at least one day after a prior administration, or at least two days, at least three days, at least four days, at least five days, or at least six days after a prior administration. In some embodiments, a subsequent administration is provided at least one week after a prior administration, or at least two weeks, at least three weeks, or at least four weeks after a prior administration. In some embodiments, a subsequent administration is provided at least one month, at least two months, at least three months, at least six months, or at least twelve months after a prior administration.

The amount of the disclosed compositions administered to a subject will vary from subject to subject, depending on the nature of the disclosed compositions and/or formulations, the species, gender, age, weight and general condition of the subject, the mode of administration, and the like. Effective dosages and schedules for administering the compositions may be determined empirically, and making such determinations is within the skill in the art. The dosage ranges for the administration of the disclosed compositions are those large enough to produce the desired effect (e.g., to alter insulin levels). The dosage should not be so large as to outweigh benefits by causing adverse side effects, such as unwanted cross-reactions, anaphylactic reactions, and the like, although some adverse side effects may be expected. The dosage can be adjusted by the individual clinician in the event of any counterindications. Generally, the disclosed compositions and/or formulations are administered to the subject at a dosage of active component(s) ranging from 0.1 µg/kg body weight to 100 g/kg body weight. In some embodiments, the disclosed compositions and/or formulations are administered to the subject at a dosage of active component(s) ranging from 1 µg/kg to 10 g/kg, from 10 µg/kg to 1 g/kg, from 10 µg/kg to 500 mg/kg, from 10 µg/kg to 100 mg/kg, from 10 µg/kg to 10 mg/kg, from 10 µg/kg to 1 mg/kg, from 10 µg/kg to 500 µg/kg, or from 10 µg/kg to 100 µg/kg body weight. Dosages above or below the range cited above may be administered to the individual subject if desired.

The subject can be any mammalian subject, for example a human, dog, cow, horse, mouse, rabbit, etc. In some embodiments, the subject comprises a small molecule which can be sensed and responded to by the particle.

In some embodiments, the disease is glycemic imbalance. In some embodiments, the disease is hyperglycemia. In some embodiments, the disease is diabetes.

In some embodiments, the method treats hyperglycemia by reducing blood glucose levels. For example, the method can treat hyperglycemia by releasing the therapeutic agent, wherein the therapeutic agent reduces blood glucose levels. In some embodiments, the method increases insulin levels.

In some embodiments, the method avoids hypoglycemia by avoiding reducing blood glucose levels to hypoglycemic levels. For example, the method can avoid hypoglycemia by avoiding further releasing the therapeutic agent once the desired glucose levels are achieved.

Also disclosed herein are methods to release insulin to an environment comprising increased glucose levels, the method comprising exposing to the environment a particle comprising an inner liposomal vesicle (ILV) encapsulating insulin, an outer liposomal vesicle (OLV) encapsulating the ILV, a membrane fusion-promoting agent, and a pH-altering agent. Upon exposure of the particle to the environment comprising increased glucose levels, the particle can release insulin encapsulated within the ILV. Release can occur by mechanisms described herein, for instance by OLV-ILV fusion and subsequent "exocytosis" of encapsulated insulin.

The particle can be any particle disclosed herein.

The environment can be an artificial environment such as a laboratory assay. Alternatively, the environment can comprise cells and/or tissues (e.g., in situ experiments or assays). In some embodiments, the environment can comprise a biological fluid, such blood or lymph. In some embodiments, the environment can be within a subject, for instance a human.

In some embodiments, increased glucose levels are in comparison to physiologically normal glucose levels.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1

Materials and General Methods.
Materials.
All lipids including egg phosphatidylcholine (EPC), 1,2-dioleoyl-sn-glycero-3-phosphoethanolamine (DOPE), dipalmitoylphosphatidylcholine (DPPC), 1,2-dioleoyl-snglycero-3-phosphoethanolamine-N-(7-nitro-2-1,3-benzoxadiazol-4-yl) (ammonium salt), and 1,2-dioleoyl-sn-glycero-3-phosphatidylethanolamine-lissamine-rhodamine B were purchased from Avanti Polar Lipids, Inc. All peptides were synthesized by Biochem Co., Ltd. (Shanghai, China). All DNAs were bought from DNA Technologies, Inc. (Coralville, Iowa, USA). Cholesterol, glucose oxidase, catalase, gramicidin A, methoxypolyethylene glycol maleimide (mPEG-Mal, M.W.=5000), phenylmethylsulfonyl fluoride (PMSF), n-dodecyl β-D-maltoside (DDM) and 8-hydroxypyrene-1, 3, 6-trisulphonic acid trisodium salt (HPTS) were purchased from Sigma-Aldrich. Human recombinant insulin was purchased from Life Technology. Anti-Glucose Transporter 2 antibody was purchased from AβCam (cat. # ab54460).

Instrumentation.

Circular dichroism (CD) spectra were recorded using a Jasco J-815 spectropolarimeter (Jasco Inc., Easton, Md.) while the sample cell was flushed with nitrogen. Transmission electron microscopy (TEM) images were acquired with JEOL 2000FX scanning transmission electron microscope (JEOL USA, Inc.) at 200 kV. Fluorescence measurements were carried out by using a FLS980 fluorescence spectrophotometer (Edinburgh Instruments). ELISA assays, insulin detection and cell viability analysis were conducted on Infinite 200 PRO multimode plate reader (Tecan Group Ltd., Switzerland). Confocal microscopy images were obtained with Zeiss LSM 710 confocal microscope (Carl Zeiss, Germany), and the samples were visualized using the same acquisition settings and analyzed using Zen 2011 software (Carl Zeiss). Confocal microscopy movie was recorded with Zeiss LSM 880 Airyscan. Cryogenic TEM images were acquired with the help of ICBR Electron Microscopy at the University of Florida. The blood glucose levels in mice were monitored using the Clarity GL2Plus glucose meter (Clarity Diagnostics, Boca Raton, Fla.). Cryo-SEM images were obtained with JEOL 7600F equipped with Gatan Alto (JEOL USA, Inc.). After cryo-facture of the larger liposomes, the sample was then sublimed at −95° C. for 5 mins under $10^{-6}$ mbar vacuum. This step was used to reveal the internal fine structure by subliming the ice crystals. The darker background outside the larger liposomes was ice. From the differences in brightness, the ice and the small liposome nanoparticles can be distinguished.

Statistical Analysis.

Biological replicates were used in all experiments. Student's t-test or ANOVA were utilized to determine statistical significance between different groups. A P value<0.05 was considered to be statistically significant. All statistical analyses were performed using Origin 8.5. No statistical methods were used to pre-determine the sample size of the experiments.

Design and Synthesis of Artificial β Cells (AβCs).

Synthesis of PEG Shield.

Figure 6:
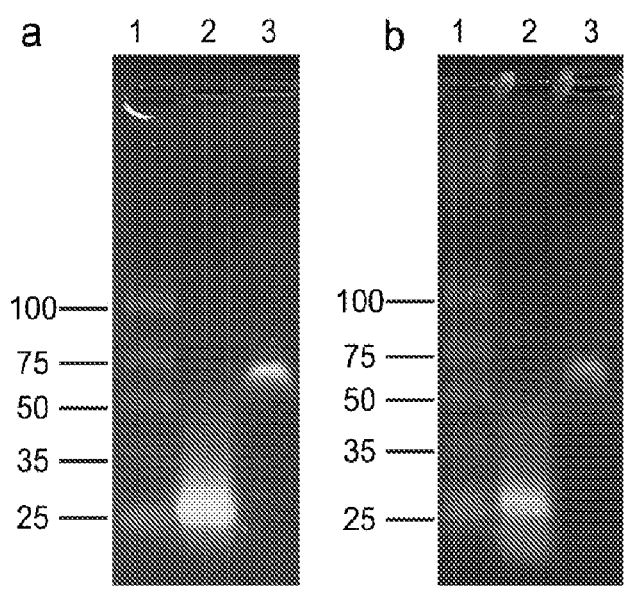
FIG. 6 is a DNA gel electrophoresis photograph. a, Agarose (2%) electrophoresis of DNA ladder (lane 1), cytosine-rich DNA (CDNA, lane 2) and $PEG_{5000}$ conjugated CDNA (lane 3); b, Agarose (2%) electrophoresis of DNA-ladder (lane 1), control DNA1 (lane 2) and $PEG_{5000}$ conjugated DNA1 (lane 3).
Figure 7:
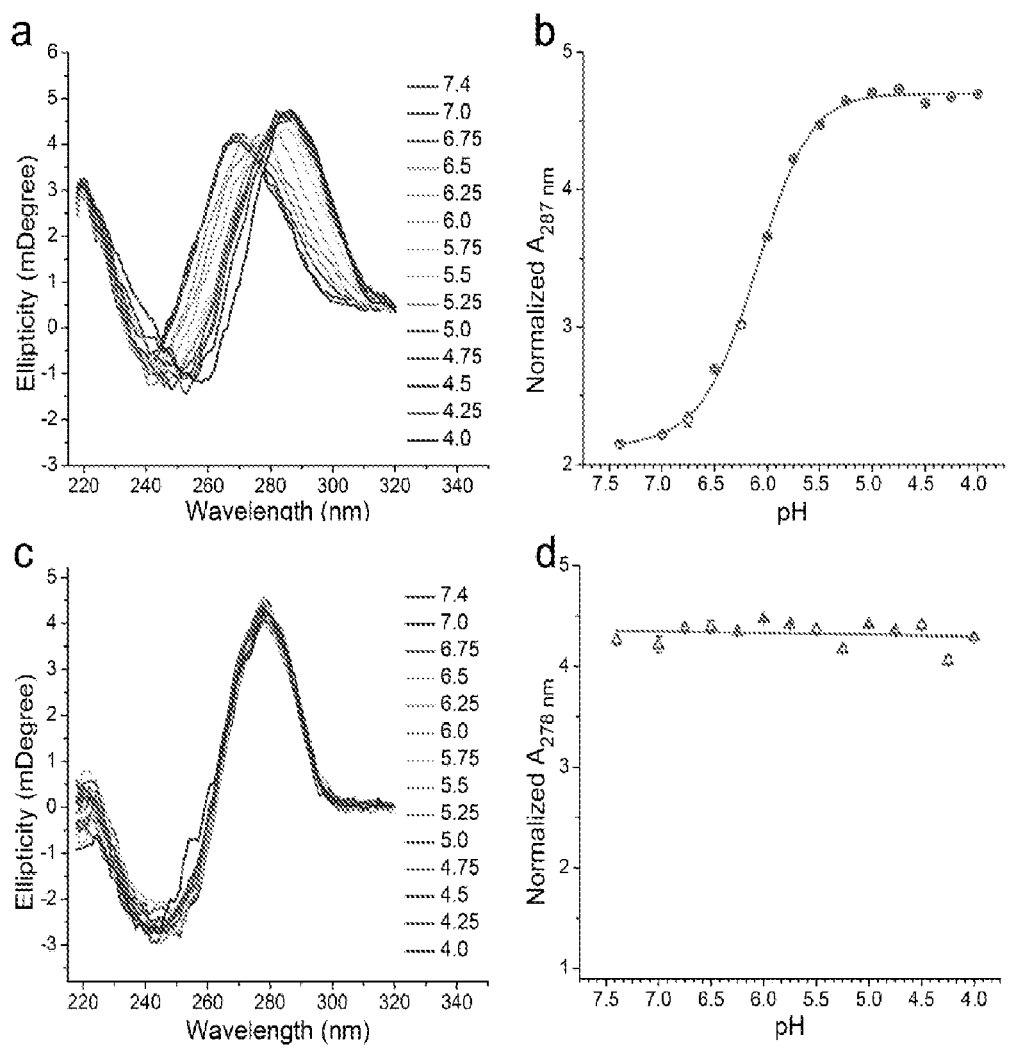
FIG. 7 is a set of graphs depicting the CD spectra of PEG-CDNA/GDNA-CH (a) and PEG-DNA1/DNA2-CH (c) that illustrate DNA conformational changes at different pH's. b, the CD intensity of the characteristic band of tetraplex DNA (summation of i-motif and G-quadruplex) around 287 nm versus different pH values while (d) shows the CD intensity of the characteristic band of duplex DNA at 278 nm versus pH values. From the results, it can be concluded that PEG-CDNA/GDNA-CH dehybridized and formed tetraplexes below pH 5.5 while the control PEG-DNA1/DNA2-CH showed no dissociation during the studied pH range. Data points represent mean±SD (n=3).

3'-thiolated cytosine (C)-rich DNA (CNDA) and mPEG-Mal solution at a DNA/mPEG-Mal molar ratio of 1/5 were mixed in HEPES buffer (1 mM, pH 7.5) and incubated for 4 h. The conjugation of PEG with CDNA (PEG-CDNA) was verified by agarose gel (1%) electrophoresis (FIG. 6a), where PEG-CDNA showed a much slower mobility than CDNA. After that, the cholesterol-ended guanine (G)-rich DNA (GDNA-CH) was mixed with PEG-CDNA to form duplexed DNA bridged PEG shield (PEG-CDNA/GDNA-CH), which had the capability to insert into liposome membranes. The fluorescently labeled DNA and non-pH-responsive DNA bridged PEG shield was prepared by the same process. The DNA bridged PEG shields were lyophilized before preparation of liposomes. The sequences of all DNAs are shown in Table 1. The conformational switch of the PEG-CDNA/GDNA-CH and non-pH-responsive DNA bridged PEG shield at different pH was studied by the CD spectroscopy (FIG. 7). From the CD spectra, no conformational variation was observed for the control DNA. However, for PEG-CDNA/GDNA-CH the characteristic peak of DNA tetraplex around 290 nm increased as the pH decreased. The CD spectra of PEG-CDNA/GDNA-CH showed that the PEG-CDNA/GDNA-CH mainly existed as duplex at and above pH 6.5, whereas the PEG-CDNA/GDNA-CH disassociated to form tetraplex at and below pH 5.5.

Preparation of Insulin-Loaded Fusogenic Small Liposomal Vesicles (ISV) Labeled with Peptide-K and PEG Shield.

Lipid stock solution was prepared in chloroform with the composition of EPC/DOPE/CH (2.5:2.5:1, w:w:w). Peptide-K (50 μM) and PEG shield (50 μM) stock solutions were prepared in chloroform/methanol (1:1, v:v) and methanol, respectively. Then a solution of lipids, peptide-K and PEG shield was prepared with final molar ratio of 95:1:4 and added to round-bottom flask. Afterwards, the solvent was evaporated by the rotary vacuum evaporator to get lipid film and the lipid film was dried under vacuum overnight. Next, insulin was dissolved in 4 mL HEPES buffer (5 mM, 150 mM NaCl, pH 7.4) and added to rehydrate the lipid film with gently vortex. A total 50 mg of insulin was used for each 100 mg of lipid. The resulting suspension was sonicated by a probe sonicator for 5 minutes with a power of 100 W and time interval of is/is to get a milky suspension. Afterwards, the suspension was extruded 10 times through polycarbonate membranes with pore size of 100 nm using an Avanti mini-extruder (Avanti Polar Lipids, Alabaster, Ala.). The free insulin was removed by centrifugation at 20,000 rpm for 60 min at 4° C. and the liposomes were washed twice. To the sedimented liposomes, 4 mL HEPES buffer was added to get the final insulin-loaded ISV. The loading efficiency of insulin was calculated as the ratio of the concentrations of the liposome-associated insulin to the initially added insulin and it was approximately 36.4% by a Coomassie Plus protein assay. ISV without insulin or peptide-K were prepared by the same manner and used in control experiments.

Preparation of Interdigitated DPPC Bilayer Sheets (Kisak, E., et al., Langmuir 18, 284-288 (2002); Boni, L. T. et al., BBA-Biomembranes 1146, 247-257 (1993); Ahl, P. et al., BBA-Biomembranes 1195, 237-244 (1994)). DPPC dissolved in chloroform and peptide-E dissolved in chloroform/methanol (1:1, v:v) at a molar ratio of 98:2 were added to a round-bottom flask. After the solution was evaporated to form thin lipid films, HEPES buffer was added and the film was hydrated at 60° C. The final lipid concentration was 50 mg/mL. Afterwards, the suspension was sonicated at 60° C. for 5 min with a power of 100 W and time interval of 1 s/1 s to get a milky suspension. Then, the solution was extruded sequentially through syringe filters with pore size of 200 and 100 nm for 10 times respectively at 60° C. to get liposomes with size less than 100 nm (FIG. 10a, b). Afterwards, interdigitated sheets were formed by adding ethanol dropwise to 0.5 mL of the DPPC liposomes; the final concentration of ethanol was typically 3M. The solution was allowed to sit for 2 h to ensure complete interdigitation. After that, the resulting sheets were washed thrice by adding 3 mL HEPES buffer to remove excess ethanol, followed by centrifugation at 5000 rpm and removal of supernatant. The obtained sheets were characterized by Cryo-SEM (FIG. 10c) and transmission electron microscopy (FIG. 10d).

Building AβCs:

To encapsulate ISVs inside the outer large liposomal vesicles (OLVs), 0.5 mL of the above prepared ISVs, 6 mg glucose oxidase and 1.5 mg catalase were added to one batch of the above prepared DPPC sheets. Then, the mixture was heated at 45° C. (above the main transition temperature of DPPC) for 20 min under gentle stirring to drive the sheets to close around ISV and glucose oxidase/catalase to form the vesicles-in-vesicle superstructures (ISVs@OLV) (Kisak, E., et al., Langmuir 18, 284-288 (2002); Boni, L. T. et al., BBA-Biomembranes 1146, 247-257 (1993); Ahl, P. et al., BBA-Biomembranes 1195, 237-244 (1994)). The free ISV and glucose oxidase/catalase were removed by centrifugation at ~2000 rpm and washed twice. All the supernatant was collected and ultracentrifuged to measure the loading efficiency of ISV and glucose oxidase/catalase. The amount of the ISV encapsulated inside OLV was determined indirectly by measuring the amount of insulin in the free ISV. About 52.8% of ISV were encapsulated. The unencapsulated glucose oxidase/catalase was detected by Bradford staining to measure the protein amounts in the supernatant after ultracentrifugation. About 45.2% of glucose oxidase/catalase were encapsulated. After that, glucose transporter 2 (expression and purification methods shown below) was reconstituted onto the OLV according to a previously reported method (Kasahara, M. et al., Proc. Natl Acad. Sci. USA 73, 396-400 (1976)). Approximately 1 mg glucose transporter 2 in was mixed with 1/5 of the centrifuged ISVs@OLV in 0.5 mL HEPES buffer. After mixing homogeneously, the suspension in a tube was quickly frozen in liquid nitrogen for 5 min and subsequently sonicated for 20 or 30 s in a bath sonicator. The suspension was centrifuged at ~2000 rpm and washed twice to remove free glucose transporter 2. The reconstitution efficiency of glucose transporter 2 was determined as 82% by the glucose transporter 2 ELISA Kits. Finally, the proton channel Gramicidin A (GA) at different GA-to-DPPC ratios in DMSO solution was added to the suspension of glucose transporter 2-reconstituted ISVs @ OLV used for the following experiments.

Glucose Transporter 2 Expression and Purification.

The cDNA encoding mouse glucose transporter 2 (Origene, Genbank accession #NM_031197) was amplified and cloned into the BamH I and Hind III sites of pET-28a (Novagen, see Supplementary Note 1 for full plasmid sequence). The constructed plasmid was transfected into $E.$ $coli$ Rosetta (DE3) pLysS cells for glucose transporter 2 expression. The $E.$ $coli$ cells were cultured in lysogeny broth supplemented with kanamycin and chloromycetin, protein expression was induced with 0.5 mM isopropyl β-D-1-thiogalactopy-ranoside. The cells were collected by centrifugation and re-suspended in Buffer A (20 mM Tris-HCl pH 8.0, 0.15 M NaCl, 10 mM imidazole, 1 mM PMSF, 5% glycerol, 0.4 mg/mL DNase I, 2% DDM and 0.5 mg/mL lysozyme). The suspension was incubated at 25° C. for 0.5 h and kept on ice for another 0.5 h. After brief sonication, cell debris was removed by centrifugation (20000×g, 10 min). The clear supernatant was added to a column filled with Ni-NTA resin (Qiagen). After washing the column with Buffer B (20 mM Tris-HCl, pH 8.0, 25 mM imidazole, 5% glycerol, 0.15 M NaCl and 0.05% DDM), glucose transporter 2 was eluted with Buffer C (20 mM Tris-HCl, pH 8.0, 0.15 M NaCl and 500 mM imidazole, 5% glycerol and 0.05% DDM). Purified glucose transporter 2 was quantified by the Bradford staining (Bio-Rad) and the purity was analyzed by SDS-PAGE (FIG. 13).

Biochemical Processes Inside AβCs.

Glucose Sensing and Metabolism by AβCs.

The fluorescence intensities of HPTS (514 nm emission, 406 ($I_{406}$) and 460 ($I_{460}$) nm excitation) were strongly dependent on the degree of ionization of the 8-hydroxyl group ($pK_a$=7.2) and hence on the pH of the medium. The intensities of $I_{406}$ and $I_{460}$ increased linearly with increasing HPTS concentrations up to 2 μM (Tunuguntla, R. H., et al., Nat. Nano. 11, 639-644 (2016); Kano, K. et al., BBA-Biomembranes 509, 289-299 (1978)). The titration curve of HPTS (0.5 μM) at different pH (HEPES buffer, 5 mM, 100 mM NaCl) was measured as shown in FIG. 14$a$. For glucose sensing, HPTS was loaded with ISV/GOx/CAT inside the OLV simultaneously during the encapsulation process and was used as the pH probe to measure the pH variation inside AβC as induced by glucose uptake, glucose oxidation and proton efflux. To keep a physiologically-relevant and constant external glucose concentration, 100 μL HEPES buffer containing HPTS loaded AβCs and glucose at different concentrations were added into the cup of a Slide-A-Lyzer™ MINI Dialysis Device (2K) and 1.5 mL isotonic solution containing the same concentration of glucose was added to the tube. After that, the Mini Dialysis Device was gently shaken at 37° C. At predetermined time intervals, 30 μL of the solution in the cup was taken out and the fluorescence intensities at 510 nm excited by 400 and 450 nm were detected. The pH values inside AβC were calculated using the titration curve shown in FIG. 14$b$. After measurement, the solution was returned back to the cup of Min Dialysis Device. For the glucose concentration switch experiments, AβC was first incubated at high glucose concentrations to reach equilibrium, and then the test of AβC's ability towards sensing changed glucose levels started. After each switch, the inner pH was measured until reaching equilibrium and then the AβCs were centrifuged and then re-suspend in another glucose solution. The cycles were repeated several times. 'Signal Transduction' Inside AβC.

The PEG shield attachment to and dissociation from the ISV surface triggered by pH variation induced by glucose metabolism was investigated. As for AβC, there were proteins or peptides that also had CD signals, fluorescence resonance energy transfer (FRET) method was alternatively applied to monitor this process by labeling fluorescent dye (tetramethylrhodamine, DNA-donor) onto CDNA and quencher (IAbRQ, DNA-acceptor) onto GDNA (Table 1). Similar to the glucose sensing experiments, the AβC solution was taken out at predetermined time-intervals or cycle runs and the fluorescence variation of DNA-donor at different glucose concentrations was determined. To study the PEG shedding-facilitated peptide assembly of peptide-E on ISV with peptide-K on the inner surface of OLV, the FRET method was also employed by using lysine-nitrobenzofuran (peptide-donor)-modified peptide-K and lysine-5-carboxytetramethylrhodamine (peptide acceptor)-labeled peptide-E. The interaction of the peptide was determined by the quenching efficiency of the peptide-donor by the peptide acceptor at different glucose concentrations.

Membrane Fusion.

The fusion of ISV with OLV in response to different glucose concentrations was studied by a dequenching method based on FRET. Fluorescence experiments were carried out using ISV labelled with the FRET pair 1,2-dioleoyl-snglycero-3-phospoethanolamine-N-(7-nitro-2-1,3-benzoxadiazol-4-yl) (ammonium salt) (lipid-donor, 0.5 mol %), and 1,2-dioleoyl-sn-glycero-3-phosphatidyletha-nolamine-lissamine-rhodamine B (lipid acceptor, 0.5 mol %) co-labeled ISV. After incubating AβC in different glucose solutions, the recovery of lipid-donor fluorescence was detected at different time intervals. The change in lipid-donor fluorescent intensity was plotted as:

$$F(\%)=100\times(F_t-F_0)/(F_{max}-F_0)$$

where $F_0$ was the lipid-donor fluorescent intensity at t=0 before addition to glucose solution, $F_t$ was the lipid-donor fluorescent intensity measured at time t, and $F_{max}$ was the lipid-donor fluorescent intensity after disruption of the AβC in 1% (w/v) Triton X-100. Also, the fusion process was monitored by confocal laser microscopy imaging (Zeiss LSM 710). Images were taken at different time after incubation in glucose solution.

For experiments demonstrating that no hemisfusion stage existed, the outer fluorescence of lipid-donor/lipid-acceptor co-labeled ISV was bleached by incubation with sodium dithionate (FIG. 23) ( ). The excess sodium dithionate was removed by centrifugation at 20000 rpm. Then, the fusion of the inner membrane of ISV with the outer membrane of OLV was detected by an identical dequenching assay.

In Vitro Dynamic Insulin 'Secretion' from AβCs.

100 μL AβC mixed with different concentrated glucose solutions were added into the cup of a Slide-A-Lyzer™ MINI Dialysis Device (2K) and 1.5 mL isotonic solution containing the same concentration of glucose was added to the tube. After that the Mini Dialysis Device was gently shaken at 37° C. At indicated time points, 15 μL of the solution in the cup was taken out and centrifuged at 6000 rpm for 1 min. Then certain volume of the supernatant was taken out and the insulin was measured by the Coomassie Plus protein assay. The concentration was calculated with an insulin standard curve (FIG. 25). For concentrated samples, dilution to the range of the standard curve was needed. The remaining mixture was resuspended in paramount of fresh glucose solution and re-added to the cup. For pulsatile release studies, the AβC was first incubated within 400 ml/dL solution for 60 min and then was spun down by centrifugation and washed once with HEPES buffer. After that, the AβC was re-suspended in 100 mg/dL glucose solution for another 60 min. The cycles were repeated numerous times. Similarly, insulin concentration was determined using the Coomassie Plus protein assay.

In Vivo Diabetes Treatment.

Animal.

Animal experiments were performed according to the animal protocol approved by the Institutional Animal Care and Use Committee at the University of North Carolina at Chapel Hill and North Carolina State University. Streptozotocin (STZ)-induced C57BL/6 type 1 diabetic mice were purchased from the Jackson Lab. Experimental group sizes were approved by the regulatory authorities for animal welfare after being defined to balance statistical power, feasibility and ethical aspects. For all the animal studies, mice were randomly allocated to each group. The researchers were not blinded to group allocation during the animal studies, as demanded by the experimental designs.

Diabetes Treatment.

The in vivo efficacy of AβC was investigated on the STZ-induced adult diabetic mice (male, age 8 week). The blood glucose level of mice was monitored two days before 'transplantation' of the AβC using the Clarity GL2Plus glucose meter (Clarity Diagnostics, Boca Raton, Fla.) by collecting ~3 μL blood from the tail vein, and all mice were fasted overnight before administration. To mimic β-cell transplantation, AβC was suspended into 40% PF127 solution and subcutaneously injected into the dorsum of diabetic mice to form a thermogel (FIG. 30). A total of 300 μL of AβC/PF127 in PBS buffer or other control mixture was subcutaneously injected into the dorsum of mice with an insulin dose of 50 mg/kg after anesthesia with isoflurane. Five mice with stable hyperglycemic state were chosen for each group to 'transplant' AβC, AβC$_{(no\ insulin)}$, control AβCs that either lacking glucose sensing machinery (GSM) or membrane fusion peptides (AβC$_{(no\ GSM)}$ and AβC$_{(no\ PE/PK)}$). The blood glucose levels were monitored over time (every 15 min or 1 h for the first 12 h after administration and once per day in the following days) until returning to stable hyperglycemia. To confirm the bioactivity of the released insulin, insulin solution (20 μg of native insulin or insulin released from AβC at 400 mg/dL glucose for 6 h.) was subcutaneously injected into the dorsum of diabetes mice. To measure the plasma insulin level in vivo, 25 μL of blood sample was collected from the tail vein of mice at indicated time points. The plasma was isolated and stored at −20° C. until assay. The plasma insulin concentration was measured using a Human Insulin ELISA kit according to the manufacturer's protocol (Calbiotech, USA). A series of glucose tolerance tests were conducted at 24, 36 and 48 h post transplantation to confirm the effective release of insulin from the AβCs in response to the glucose challenge. Briefly, glucose solution in PBS was intraperitoneally injected into all mice at a dose of 1 g kg$^{-1}$. The blood glucose level was closely monitored for 120 min after injection. The results of glucose tolerance tests on healthy mice were used as control.

Cell Culture.

HeLa cells were obtained from Tissue Culture Facility of UNC Lineberger Comprehensive Cancer Center. The cells were cultured in Dulbecco's Modified Eagle Medium (Gibco, Invitrogen) with 10% (v:v) fetal bovine serum (Invitrogen), 100 U ml$^{-1}$ penicillin (Invitrogen) and 100 mg ml$^{-1}$ streptomycin (Invitrogen) in an incubator (Thermo Scientific) at 37° C. under an atmosphere of 5% $CO_2$ and 90% relative humidity. Cells were tested every three months for potential mycoplasma. Re-authentication of cells was not performed after receipt.

Biocompatibility Evaluation.

The cytotoxicity of AβC$_{(no\ insulin)}$ was examined on HeLa cells by a 3-(4, 5)-dimethylthiahiazo(-z-yl)-3,5-di-phenytet-razoliumromide (MTT) assay. Briefly, HeLa cells were seeded at a density of 5000 cells well$^{-1}$ (200 μL total volume well$^{-1}$) in 96-well plate. After 24 h, AβC$_{(no\ insulin)}$ at indicated concentrations was added and cells were further incubated for 24 h. Thiazolyl blue solution (5 mg mL$^{-1}$) was added into wells (final concentration: 0.5 mg mL$^{-1}$) and incubated with cells for 4 h. After removing the culture media, the purple formazan crystal was dissolved in 200 μL of DMSO. The absorbance at 570 nm, which is directly proportional to the viable cell number, was measured on the Infinite 200 PRO multimode plate reader (Tecan Group Ltd., Switzerland).

To evaluate the in vivo biocompatibility of AβC, four weeks after injection of AβC/PF127, the diabetes mice were euthanized via $CO_2$ asphyxiation, and the injected materials and surrounding tissues were excised. The tissues were then fixed in 10% formalin, embedded in paraffin, cut into 5 μm sections, and stained using hematoxylin and eosin for histological analysis. During the same time, the body weight of the diabetes mice in each group was recorded. Moreover, for immune analysis, representative inflammatory factors, such as TNF-α, IL-β and IL-6, in the serum of each group were measured by ELISA

TABLE 1

DNA sequences used for synthesis of PEG shield.

| pH-responsive DNA | CDNA | 5'-CCC TTA CCC TTA CCC TTA CCC TTT TTT-SH-3' | SEQ ID NO: 3 |
|---|---|---|---|
| | TAMRA-labeled CDNA | 5'-CCC TAA CCC TAA CCC TAA CCC T/i5-TAMK/T TTT T-SH-3' | SEQ ID NO: 4 |

TABLE 1-continued

DNA sequences used for synthesis of PEG shield.

|  |  |  |  |
|---|---|---|---|
|  | *GDNA | 5'-GGG TTA GGG TTA GGG TTA GGG TTT TTT-CH-3' | SEQ ID NO: 5 |
|  | IAbRQ-labeled GDNA | 5'-IAbRQ-GGG TTA GGG TTA GGG TTA GGG TTT TTT-CH-3' | SEQ ID NO: 6 |
| Non-pH-responsive DNA | DNA1 | 5'-CTC TCA CAC TCA CTC TCA CGC TTT TTT-SH-3' | SEQ ID NO: 7 |
|  | TAMRA-labeled DNA1 | 5'-CTC TCA CAC TCA CTC TCA CGC T/i5-TAMK/TT TTT-SH-3' | SEQ ID NO: 8 |
|  | DNA2 | 5'-GCG TGA GAG TGA GTG TGA GAG TTT TTT-CH-3' | SEQ ID NO: 9 |
|  | IAbRQ-labeled DNA2 | 5'-IAbRQ-GCG TGA GAG TGA GTG TGA GAG TTT TTT-CH-3' | SEQ ID NO: 10 |

Results

Construction of the AβCs.

Figure 8:
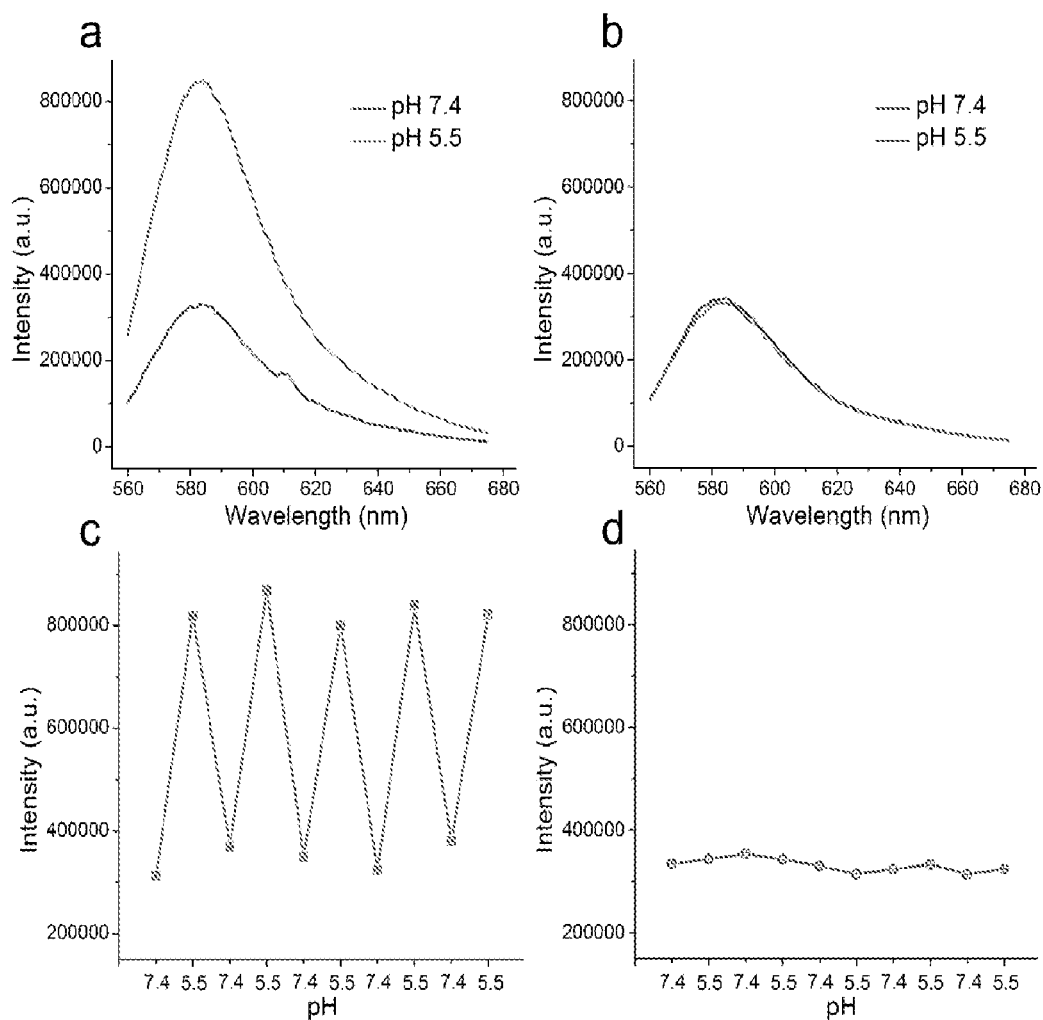
FIG. 8 is a set of graphs depicting reversible, pH-controlled attachment/detachment of PEG shield on the ISV surface studied using a fluorescent resonance energy transfer (FRET) assay. Fluorescent spectra of (a) $PEG_{5000}$-conjugated C-rich DNA (labeled with tetramethylrhodamine, DNA-donor)/cholesterol-ended G-rich DNA (labeled with IAbRQ, DNA-acceptor)-inserted ISVs and (b) $PEG_{5000}$-

To implement the AβC design, insulin-loaded ISVs were first prepared via the classic lipid film hydration method (Mo, R., et al., Angew. Chem. Int. Ed. 53, 5815-5820 (2014)), where 4 mol % PEG-CDNA/GDNA-CH (FIG. 6) and 1 mol % peptide-K were inserted into the membrane by in situ modification. FIG. 1b presents a transmission electron microscopy image of the ISVs, which have an average diameter of 50 nm. Due to the conformational switch between double-stranded duplex DNA and intramolecular tetraplex structures at physiological pH and acidic pH (pH<6.0, FIG. 7) (Zhao, C., et al., Chem. Eur. J. 17, 7013-7019 (2011); Li, X., et al., Proc. Natl Acad. Sci. USA 103, 19658-19663 (2006)), the PEG shield was reversibly attached to and disassociated from ISV, as shown by the fluorescent resonance energy transfer (FRET) method (FIG. 8). The peptide-K and the peptide-E were each designed with three features: a transmembrane domain, a spacer, and a recognition motif (FIG. 9a), mimicking the membrane fusion SNARE polypeptides (Marsden, H. et al., Chem. Soc. Rev. 40, 1572-1585 (2011); Lygina, A. et al., Angew. Chem. Int. Ed. 50, 8597-8601 (2011); Robson Marsden, H., et al., Chem. Int. Ed. 48, 2330-2333 (2009); Meyenberg, K., et al., Chem. Commun. 47, 9405-9407 (2011); Tomatsu, I. et al., J. Mater. Chem. 21, 18927-18933 (2011); Kong, L., et al., Angew. Chem. Int. Ed. 55, 1396-1400 (2016); Gong, Y., et al., J. Am. Chem. Soc. 130, 6196-6205 (2008); Chan, Y. et al., Proc. Natl Acad. Sci. USA 106, 979-984 (2009); Steinmetz, M. et al., Proc. Natl Acad. Sci. USA 104, 7062-7067 (2007)). As such, heterodimeric coiled coils driven by the electrostatic and hydrophobic interactions of the heptad repeats in the recognition part were formed upon mixing peptide-E and peptide-K (FIG. 9b). Insertion of the pH-responsive PEG shield on ISVs, an interaction between peptide-E and peptide-K occurred only in the unshielded state (Tomatsu, I. et al., J. Mater. Chem. 21, 18927-18933 (2011); Kong, L., et al., Angew. Chem. Int. Ed. 55, 1396-1400 (2016)). ISVs and glucose oxidase/catalase were encapsulated into OLV decorated with 2 mol % peptide-K by heating interdigitated dipalmitoylphosphatidylcholine sheets above the gel-liquid phase transition temperature (FIG. 10) (Kisak, E., et al., Langmuir 18, 284-288 (2002)). Annealing the interdigitated phospholipid sheets led to the formation of closed compartments with large size and high internal volume (Kisak, E., et al., Langmuir 18, 284-288 (2002)), simultaneously entrapping enzymes and ISVs at high efficiency. Catalase was added to decompose the undesired hydrogen peroxide and regenerate oxygen to facilitate glucose oxidation (FIG. 11). The resulting vesicles-in-vesicle superstructures with an overall size of ~1-5 μm was shown via cryogenic scanning electron microscopy (Cryo-SEM) image (FIG. 1c, d), cryogenic transmission electron microscopy image (FIG. 12), and a confocal microscopy movie. The localization glucose oxidase/catalase inside the cavities of OLV was demonstrated by confocal laser microscopy imaging (CLSM; FIG. 1e). Next, glucose transporter 2, which was expressed and purified from E. coli (FIG. 13a), was reconstituted into the OLV membrane by a freeze-thaw sonication method. The presence of glucose transporter 2 on the OLV membrane was verified by Western blotting (FIG. 1f, FIG. 13b) and CLSM imaging (FIG. 1g). Finally, gramicidin A, a membrane-spanning channel capable of conducting protons at very high flux rates (Tunuguntla, R. H., et al., Nat. Nano. 11, 639-644 (2016)), was inserted into the membrane of OLV, as shown in the CLSM image by incorporating lysine-5-carboxyfluorescein-ended gramicidin (FIG. 1h).

Biochemical Processes Inside AβCs.

Figure 2:
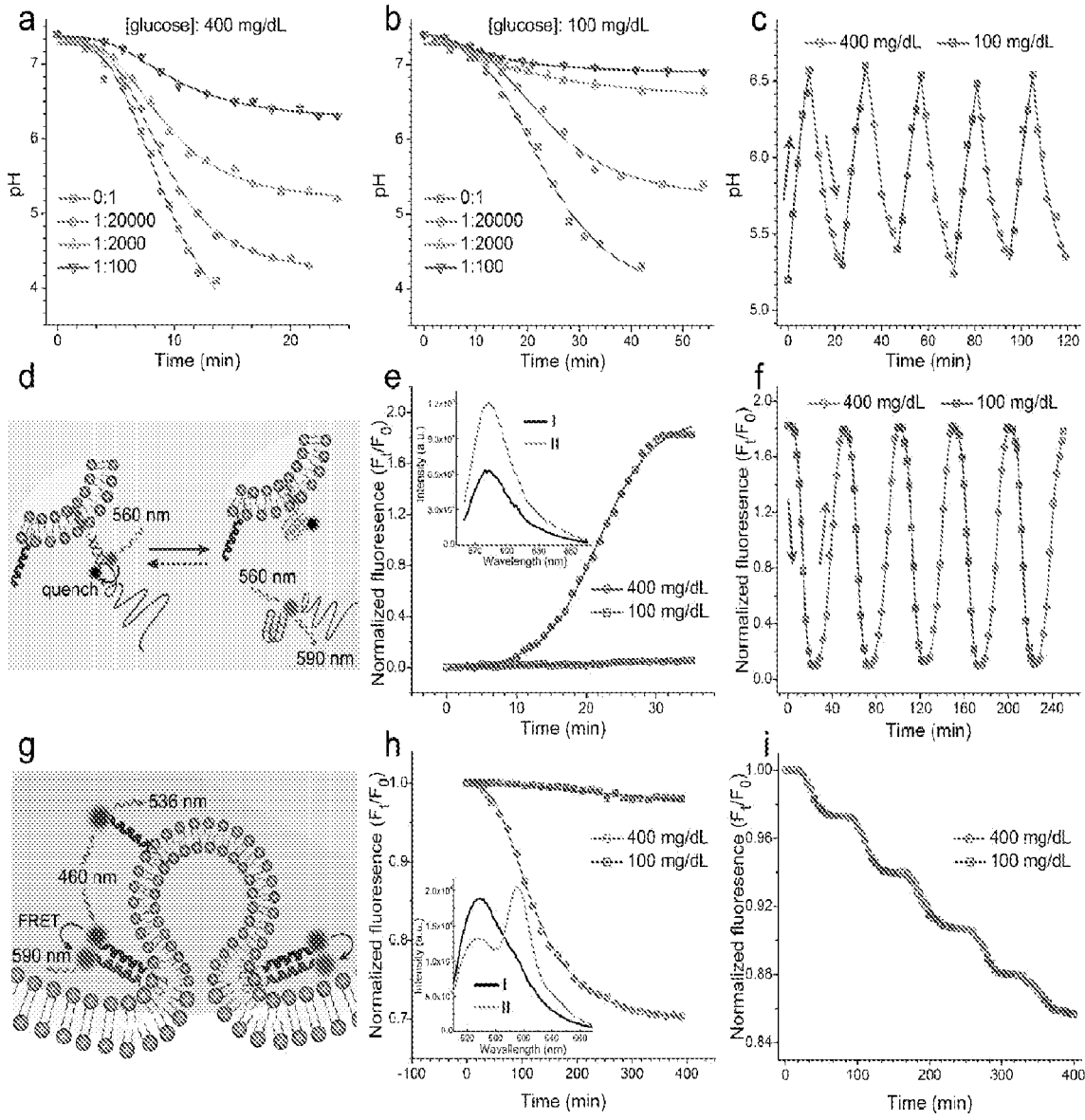
FIG. 2 is a set of graphs and schematics depicting biochemical processes inside AβCs. a-c, Glucose sensing ability of AβCs. pH variation inside AβCs in 400 (a) and 100 (b) mg/dL glucose solutions. The ratios represent the relative amount of gramicidin A to that of dipalmitoylphosphatidylcholine lipid. c, Reversible pH variation induced by alternatively switching environmental glucose concentrations. d-i, 'Signal transduction' inside AβCs to control PEG deshielding and peptide assembly. d, Schematic for reversible PEG association and disassociation tuned by glucose metabolism. PEG-CDNA was labeled with the tetramethylrhodamine (DNA-donor), while GDNA-CH was labeled with IabRQ (DNA-acceptor). e, FRET assay to study the dehybridization of the pH-sensitive DNA duplex which bridges the PEG shield and the ISV surface at different glucose concentrations. f, Reversible quenching and recovery of the fluorescence of DNA-donor to prove the reversible attachment and detachment of the PEG shield in high and low glucose solutions. g, Schematic illustration of quenching of nitrobenzofuran (NBD, peptide-donor) on peptide-K by tetramethylrhodamine (TRMRA, peptide-acceptor) on peptide-E induced by peptide assembly after PEG dissociation. h, FRET assay to study the interactions of peptide-E and peptide-K at different glucose concentrations. In Panel e and h, $F_0$ and $F_t$ represent the fluorescence intensity measured before and at time t after addition into glucose solutions; inset: (I) and (II) respectively show the fluorescence spectra of the AβCs before and after incubation in 400 mg/dL glucose solution. i, Step decrease in fluorescence intensity of peptide-donor by switching the glucose concentrations. Data points represent mean±SD (n=3).

To determine the glucose sensing ability of the AβCs, the glucose transport machinery was coupled to an interior enzymatic oxidation scheme and a pH-sensitive dye (FIG. 14). The biochemical process was monitored by fluorescence measurements (FIG. 2a-b, FIG. 15a-b). At a fixed lipid/glucose transporter/glucose oxidase ratio, the inner pH level was dependent on the external glucose concentration as well as the amount of added gramicidin. At the same gramicidin level, the pH decrease was significantly faster at 400 mg/dL glucose (a typical hyperglycemia level) than that at 100 mg/dL (a normoglycemia level). Moreover, similar pH variations but with relatively slower kinetics were observed at modest hyperglycemic levels (300 and 200 mg/dL). Glucose uptake by glucose transporter was confirmed in control systems with no glucose transporter present as well as in the presence of the inhibitor-cytochalasin B (FIG. 16). Given that glucose transporter 2 has a $K_m$ of about 15-20 mM (Efrat, S., Nat. Genet. 17, 249-250 (1997)) and glucose oxidase has a $K_m$ of about 33-100 mM, the difference in pH decline was attributed to the different glucose transport rates associated with high and low glucose concentrations. When the glucose concentration was held constant, inner pH was inversely correlated to the content of gramicidin; the more gramicidin was inserted, the faster protons were pumped out of the AβCs. In control systems where no gramicidin was inserted, the final pH at 100 mg/mL was similar to that at hyperglycemic levels, although the former decreased slower, indicating the necessity of gramicidin for tuning proton efflux to distinguish high and low glucose concentrations. The maximum pH-change therefore relied on the overall kinetics of glucose uptake, glucose oxidation and proton efflux. For the following studies, AβCs with gramicidin-to-lipid ratio of 1:2000 having capacity to maintain pH<5.6 at hyperglycemic level and pH>6.5 at normoglycemia level were selected. In this system, pH inside the AβC was reversed in response to adjustment of glucose concentration (FIG. 2c, FIG. 15c-d). Notably, fast response in switching pH was due to the fact that the diffusion of intermediates was minimized since all the biochemical processes were confined in a micron-scale space (Matsumoto, R. et al., Phys. Chem. Chem. Phys. 12, 13904-13906 (2010)). Such unique properties facilitate the artificial system's ability to act like natural β cells in terms of precisely sensing graded glucose levels.

Next, 'signal transduction' inside AβCs including the steric PEG deshielding and the subsequent peptide-E/peptide-K assembly was investigated. The disassociation of the PEG shield induced by glucose metabolism was confirmed via a FRET assay (FIG. 2d). The emission at 590 nm of the tetramethylrhodamine (DNA-donor) on PEG-CDNA, which was initially quenched by IAbRQ (DNA-acceptor) on GDNA-CH, gradually increased in 200-400 mg/dL glucose solutions, whereas almost no change was observed for that in 100 mg/dL glucose solution (FIG. 2e, FIG. 17a). Due to the slow kinetics for pH variation at modest hyperglycemic levels, the corresponding changes in PEG deshielding took a relatively longer time to initiate in 200 and 300 glucose solutions. A control study of a pair of randomly sequenced complementary DNA strand generated no fluorescence recovery at either high or low concentrations over time (FIG. 18). Furthermore, reversible association and disassociation of the PEG-CDNA was observed when the glucose concentrations were cyclically varied between high glucose levels and 100 mg/dL (FIG. 2f, FIG. 17b-c), indicating that the conformational conversion at high glucose levels induced the duplex dehybridization and hence the detachment of the PEG shield.

Next the pairing of peptide-K on ISV with the peptide-E on OLV was studied. Because signals of other peptides/proteins prohibited the use of circular dichroism techniques, FRET experiments were used (FIG. 2g). As shown in FIG. 2h and FIG. 19a, the fluorescence of nitrobenzofuran on peptide-K (peptide-donor) was readily quenched by the tetramethylrhodamine (peptide-acceptor) on peptide-E at high glucose concentrations, and a stepwise decrease in peptide-donor fluorescence was observed by switching the glucose concentration between high glucose levels and 100 mg/dL (FIG. 2i, FIG. 19b-c). The lag at the beginning of each switch was due to the inner pH variation and the time required for the PEG shield attachment/detachment to reach equilibrium; this lag was longer in the cases of modest hyperglycemic solutions than after exposure to the high glucose concentration. Critically, no peptide interactions were detected at low glucose levels or in control groups where non-pH responsive DNA was used (FIG. 20), indicating the direct dependence of peptide assembly on the dissociation of the PEG shield from ISVs, where protons generated by glucose (signal) metabolism act as the signal mediator and the sequence-specific DNA strands act as the signal effector facilitating the precise signal transduction inside AβC to induce PEG deshielding and subsequently activate peptide assembly.

Membrane Fusion of ISV with OLV.

Figure 3:
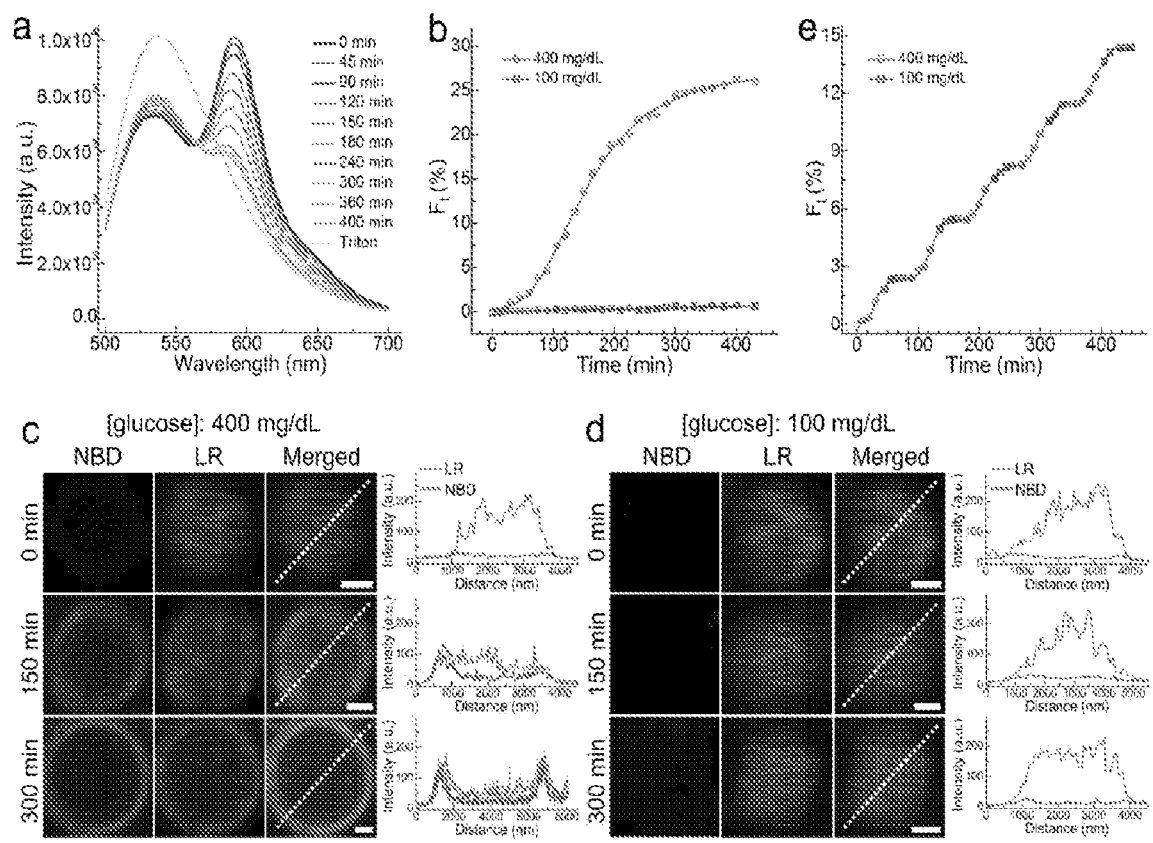
FIG. 3 shows membrane fusion of the ISV and OLV following glucose metabolism. a, Fluorescence spectra of the AβCs after incubating in 400 mg/dL glucose solution for different time. The ISV were simultaneously labeled with lipid-donor (NBD, emission $2_{max}$=536 nm) and lipid-acceptor (LR, emission $\lambda_{max}$=592 nm). Total lipid-donor fluorescence spectrum was obtained by destructing AβCs with 1% Triton X-100. b, Kinetics profiles of lipid mixing between lipid-donor/acceptor-labeled ISV and OLV in 400 mg/dL and 100 mg/dl glucose solutions, as indicated by the increase in lipid-donor emission. Each data point represents an average of triplicate measurements with standard error<10%. CLSM images showed the lipid mixing between lipid-donor/acceptor-labeled ISV and OLV in c, 400 mg/dL and d, 100 mg/dL glucose solutions after different incubation time (scale bar, 1 μm). The profiles in c and d showed the distribution of the fluorescence intensity of lipid-donor (green lines) and lipid-acceptor (red lines) along the indicated white dash lines. e, Step increase in the fluorescence of lipid-donor after alternatively changing the glucose concentrations between 400 and 100 mg/dL. Data points represent mean±SD (n=3).

With a clear 'signaling pathway', the next step was to substantiate the membrane fusion of the ISV with OLV driven by the interaction of peptide-E and peptide-K. By simultaneously incorporating lipids labelled with nitrobenzofuran (lipid-donor) and lissamine rhodamine B (lipid-acceptor) into the ISV, the efficiency of lipid mixing at different glucose concentrations was studied by a standard dequenching assay (FIG. 3a). At high glucose concentrations, continuous increase in lipid-donor emission around 536 nm was observed, indicative of dilution of the lipid-donor and lipid-acceptor dyes induced by membrane fusion (FIG. 3b, FIG. 21a). Also, as can be seen in the CLSM image (FIG. 3c), the green fluorescence of lipid-donor and red fluorescence of lipid-acceptor gradually appeared and increased on the surface of AβC in response to hyperglycemic conditions, and the fluorescence inside the AβCs gradually decreased, showing the merger of the ISV with the OLV. No obvious lipid-donor fluorescence variation was observed under normal glycemic level (FIG. 3d). In further control experiments, no recovery in lipid-donor fluorescence was detected when either peptide-E or peptide-K was omitted (FIG. 22). As peptide-E/peptide-K has been reported to be the minimal machinery that can mimic SNARE polypeptides for controlling membrane fusion (Robson Marsden, H., et al., Chem. Int. Ed. 48, 2330-2333 (2009); Meyenberg, K., et al., Chem. Commun. 47, 9405-9407 (2011)), these results therefore showed that glucose signal transduction-tuned assembly of the peptides brought the ISV and OLV closely together and transmitted the forces for promoting their fusion.

In natural beta cells, vesicles can be trafficked to the periphery of the cell membrane with the assistance of the cytoskeleton (Wang, Z. et al., J. Cell Sci. 122, 893-903 (2009)), leading to a sustainable fusion process. Lacking machinery mimicking the cytoskeleton, ISV moved randomly by Brownian motion within AβC, as shown in CLSM images (FIG. 3c-d). Both the peptide assembly and the effective contact between the randomly diffused ISVs and the OLV contributed to the observed fusion processes within AβCs (Schuette, C. et al., Proc. Natl Acad. Sci. USA 101, 2858-2863 (2004)), making the fusion process sustainable for several hours. In addition, cyclic switches in the solution glucose concentrations between hyperglycemic and normoglycemic levels resulted in stepwise increases in nitrobenzofuran fluorescence (FIG. 3e, FIG. 21b-c). Thus, based on the glucose sensing ability of AβCs and the reversible attachment of the PEG shield on ISV, this new glucose-responsive mechanism promotes fusion under high glycemic conditions and reshields the ISVs to minimize fusion at normoglycemic levels for numerous cycles.

To exclude the possibility that the fusion process was terminated at the stage of hemifusion (Lygina, A. et al., Angew. Chem. Int. Ed. 50, 8597-8601 (2011); Robson Marsden, H., et al., Chem. Int. Ed. 48, 2330-2333 (2009); Meyenberg, K., et al., Chem. Commun. 47, 9405-9407 (2011)), it was investigated whether the inner lipid layers of ISV effectively mixed with the outer lipid layers of OLV by bleaching the lipid-donor fluorophores on the outside of the ISV with sodium dithionite (FIG. 23a). Still, an increase in lipid-donor fluorescence was detected at 400 mg/dL glucose (FIG. 23b). Since the FRET effect needed the lipid-donor fluorophores inside the ISV, therefore, complete merger of both the inner and outer lipid leaflets of the membranes of ISV and OLV occurred during fusion. Such full fusion of ISV with OVL is important for the release of ISV contents outside the OLV in a way that mimics cellular exocytosis.

In Vitro Dynamic Insulin 'Secretion' from AβCs.

Figure 4:
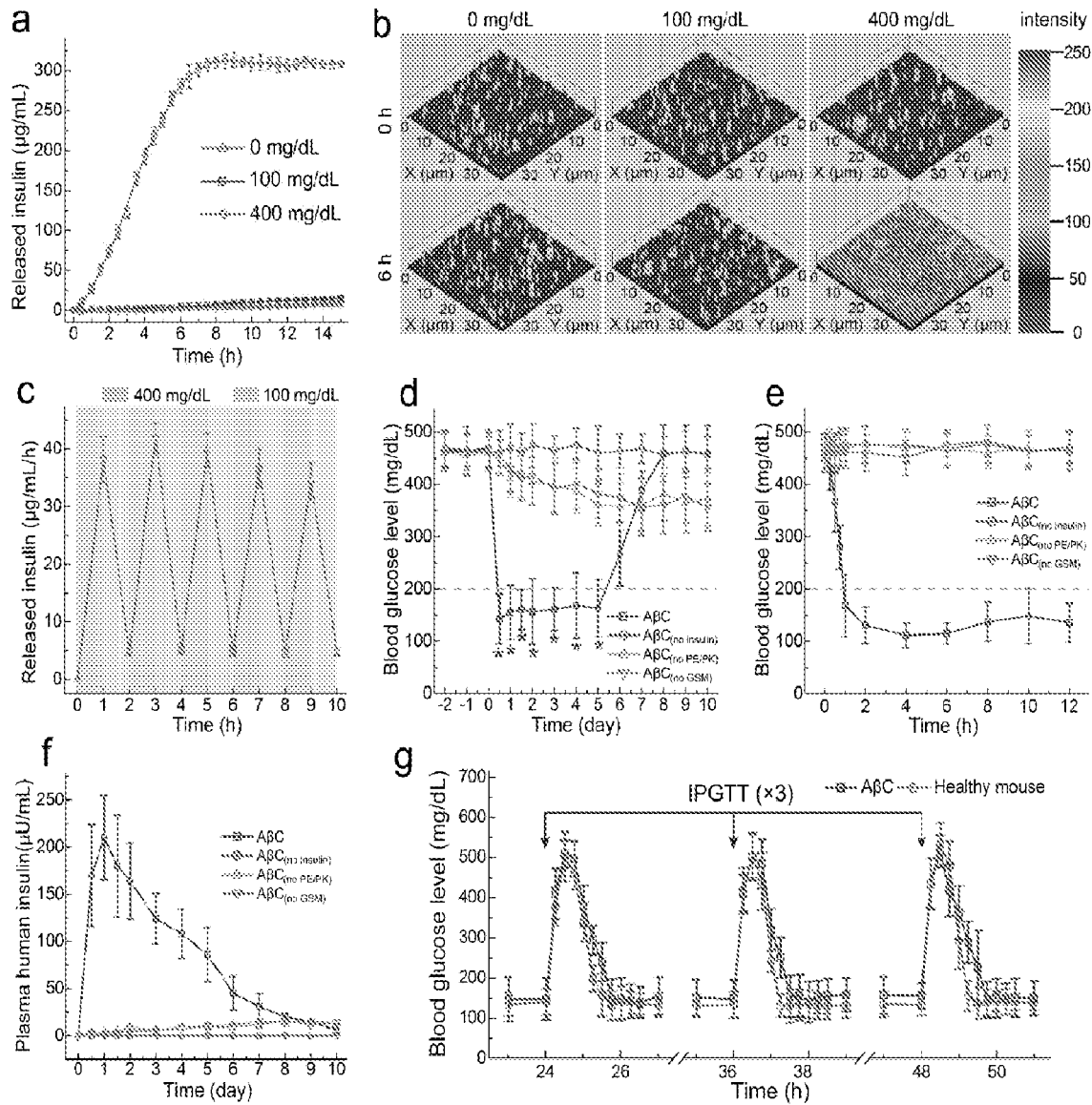
FIG. 4 shows in vitro insulin 'secretion' from AβCs and in vivo type-1diabetes treatment. a, In vitro accumulated insulin release from AβCs incubated in solutions with different glucose concentrations. Data points represent mean±SD (n=3). b, 2.5D CLSM images showed the fluorescence intensity and distribution of fluorescein labeled-insulin from AβCs before and after incubation in solutions containing different concentrations of glucose. c, Pulsatile release profile by AβCs presents the insulin release rate upon switching the glucose concentrations between 400 and 100 mg/dL. Data points represent mean±SD (n=3). d, The blood glucose levels of diabetic mice after 'transplantation' with AβCs, or control AβCs which lacked insulins ($AβC_{(no\ insulin)}$), membrane fusion peptide-E/peptide-K ($AβC_{(no\ PE/PK)}$), or glucose sensing machinery ($AβC_{(no\ GSM)}$). Data points represent mean±SD (n=5). *P<0.05 for AβCs compared with control AβCs. e, Blood glucose levels were continuously monitored in the first 12 h shown in (d). Data points represent mean±SD (n=5). f, Variation of plasma insulin concentration in diabetic mice over time after transplantation of AβC or control AβCs. Data points represent mean±SD (n=5). g, In vivo intraperitoneal glucose tolerance test (IPGTT) performed toward diabetic mice at 24, 36, and 48 h following AβC treatment in comparison to the healthy control mice. Data points represent mean±SD (n=5).
Figure 5:
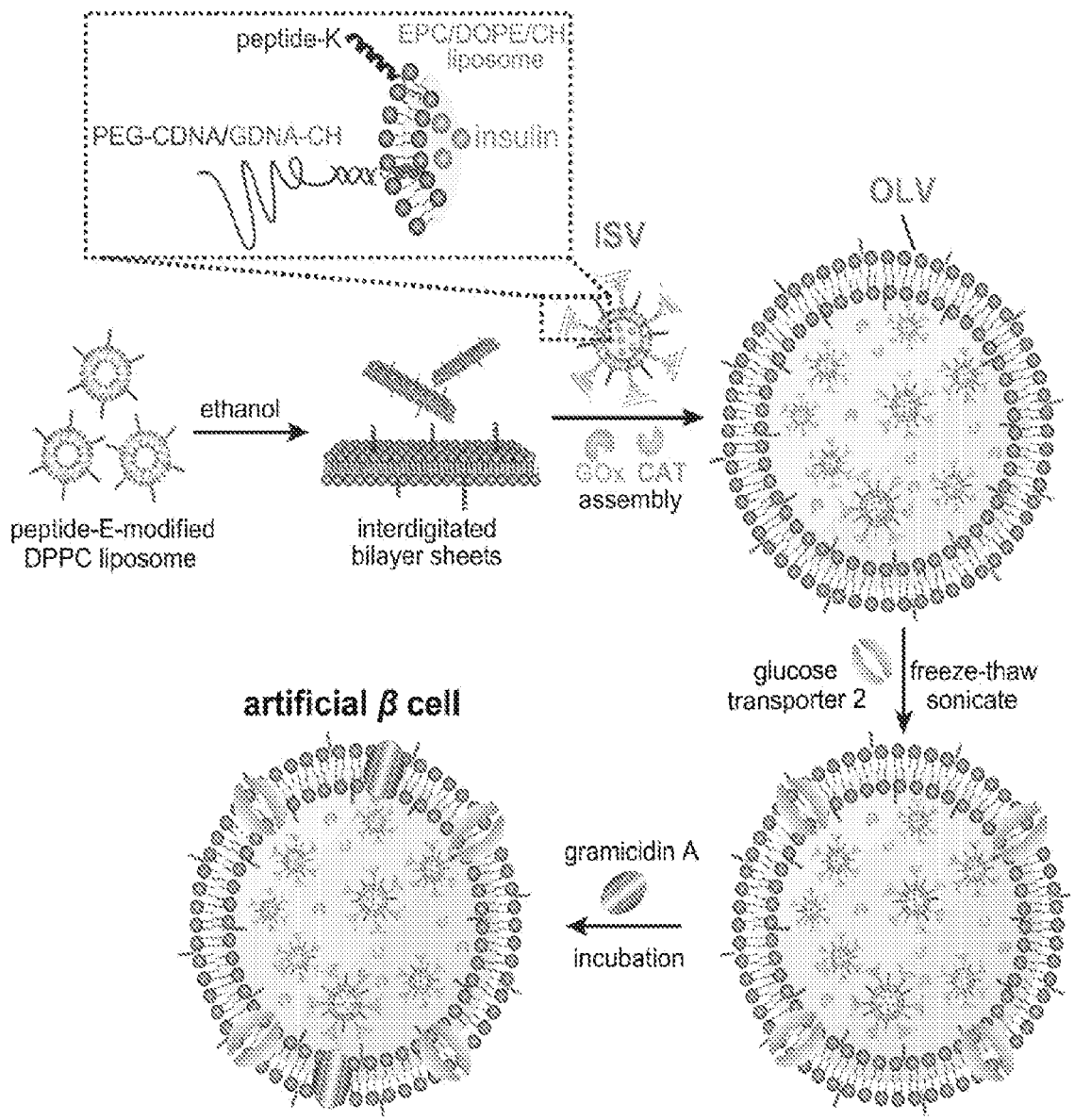
FIG. 5 is a schematic depicting the design and synthesis of the artificial β-cell. GOx, CAT, ISV and OLV are abbreviations for glucose oxidase, catalase, inner small vesicle and outer large vesicle, respectively.

In accumulated insulin release studies, a remarkably rapid insulin release was detected at hyperglycemic levels while minimal release was observed at a normal glucose level or in glucose-free buffer solution over 15 h (FIG. 4a, FIG. 24, and FIG. 25a). Notably, the fast responsiveness of AβCs to 400 mg/dL glucose compared to more conventional glucose oxidase-mediated pH decrease-dependent systems was due to the well-organized spatial confinement of all relevant biochemical processes, similar to compartmentalization in natural cells, and also reduced the interference from the buffered environment (Veiseh, O. et al., Nat. Rev. Drug. Discov. 14, 45-57 (2015); Mo, R., et al., Chem. Soc. Rev. 43, 3595-3629 (2014)). Meanwhile, the slower insulin release at modest glucose levels further contributes to dynamic response of AβCs towards different blood glucose levels. When insulin was conjugated with fluorescein isothiocyanate, CLSM imaging visualized that more homogenously distributed green fluorescence was detected for solutions containing AβCs high glucose solutions while clustered green signals remained at 100 mg/mL after incubation for 6 h (FIG. 4b, FIG. 25b), substantiating the release of insulin under hyperglycemic conditions. In control groups where AβCs lacked either glucose sensing machinery or membrane fusion peptides, very slow and non-distinguishable insulin release kinetics were observed at all glucose levels (FIG. 26a, b). Furthermore, when cyclically alternating the glucose concentrations between 400 mg/dL and 100 mg/dL every 1 h for several repetitions, a pulsatile release profile was measured for AβCs, with a maximum of 8-fold difference in insulin release (FIG. 4c). The low levels of released insulin detected after switching the glucose concentration to normoglycemic level was due to the lag between glucose metabolism, pH variation, and membrane fusion. However, no such oscillations were found for the control AβCs (FIG. 26c, d). In addition, no readily detectable insulin release was observed under mild acidic pH's (FIG. 27), avoiding non-specific activation of AβCs in dietetic mice suffering from diabetic ketoacidosis which typically leads to plasma pH level below 7.3 (KitAβChi, A. et al., Diabetes Care 32, 1335-1343 (2009)). These results illustrated that the oscillations in glucose pathway and membrane fusion of AβCs effectively contributed to the oscillatory feature of insulin release, closely mimicking the dynamic secretion features of natural β-cells.

In Vivo Type 1 Diabetes Treatment.

The ability of AβC for regulating blood glucose levels in vivo in a streptozotocin-induced type 1 diabetic mice model was examined. Prior to in vivo studies, the retention of the secondary structure and the bioactivity of the insulin released from AβCs were verified (FIG. 28 and FIG. 29). The AβCs were 'transplanted' into the subcutaneous tissues by injecting a Pluronic F-127 (PF127) solution (40 wt %) containing homogenous distributed AβCs, as PF127 is biodegradable and can quickly form a stable hydrogel at body temperature (FIG. 30) (Park, M. H., et al., Accounts Chem. Res. 45, 424-433 (2012)). The distribution and integrity of AβCs inside the hydrogels was shown via Cryo-SEM imaging (FIG. 31). In control groups, AβCs lacking insulin (AβC$_{(no\ insulin)}$), lacking the membrane fusion peptides (AβC$_{(no\ PE/PK)}$) and lacking glucose sensing machinery (AβC$_{(no\ GSM)}$) were also 'transplanted'. The blood glucose levels in mice 'transplanted' with AβC quickly declined from hyperglycemia to normoglycemia within 1 h, and after that, the blood glucose level remained normoglycemic for up to five days (FIGS. 4d and e). In contrast, mice 'transplanted' with AβC$_{(no\ insulin)}$ showed elevated blood glucose levels, excluding the possibility of blood glucose level decrease induced by catalytic consumption. For groups treated with control AβCs, elevated blood glucose levels were also observed due to the lack of self-regulated glucose sensing or membrane fusion abilities. Correspondingly, plasma insulin levels in mice treated with AβCs remained detectable over the time course while little or no plasma insulin was detected in the plasma of control groups (FIG. 4f). Intraperitoneal glucose tolerance tests were performed to further test the in vivo glucose responsive ability of AβCs at 24, 36, and 48 h post 'transplantation' (FIG. 4g). Following a spike in blood glucose level each time, mice which had received AβCs showed restoration of pre-challenge blood glucose levels at a rate comparable to that in healthy mice. Similar results were also observed on the fifth day after 'transplantation' (FIG. 32). However, no such phenomenon was observed for groups 'transplanted' with control artificial cells in the same test (FIG. 33). This in vivo responsive ability of the designed AβCs was further proved by detecting the protein release in wild-type mice that were 'transplanted' with human serum albumin-loaded AβCs 1.5 h after administration of glucose (FIG. 34).

Importantly, AβCs$_{(no\ insulin)}$ were not associated with readily detectable cytotoxicity at any of the concentrations studied (FIG. 35). Finally, the transplanted formulation including PF127 was completely degraded by four weeks post-administration, with no noticeable inflammatory region or fibrotic encapsulation (FIG. 36). At the same time, no obvious differences in body weight change were observed between treated groups and the blank group injected with PBS (FIG. 37). Also, the levels of inflammatory factors such as TNF-α, IL-1β and IL-6 in the treated groups were similar to those in control groups (FIG. 38).

DISCUSSION

Pancreatic beta-cells precisely sense blood glucose fluctuations and in turn dynamically secret insulin to maintain normoglycemia. Generating artificial cells using synthetic materials to mimic this glucose-responsive biological process in a robust manner holds tremendous promise for improving outcomes in diabetic patients. Disclosed herein is the construction of an artificial beta-cell (AβC) with a multicompartmental 'vesicles-in-vesicle' superstructure that is spatially equipped with a glucose metabolism system and membrane fusion machinery. Based on the sequential cascade of the glucose uptake, enzymatic oxidation and proton efflux, the AβCs can effectively distinguish between high and normal glucose levels via exhibiting different pH values inside the compartment of outer large liposomal vesicles. In hyperglycemic conditions, increased glucose uptake and oxidation generate a low pH (<5.6) which then induces steric deshielding of peptides tethered to the insulin-loaded inner small liposomal vesicles, such that the peptides on the small vesicles form coiled-coils with the complementary peptides anchored on the inner surface of large vesicles, subsequently bringing the membranes of the inner and outer vesicles together and triggering their fusion to 'exocytose' insulin. AβCs transplanted into chemically induced type 1 diabetic mouse model restored blood glucose levels to a normal range for at least five days, demonstrating therapeutic potential for treating diabetes.

The presently disclosed AβCs are next generation artificial cells. Different from previously reported single-compartmentalized artificial assemblies, which passively interact with biological systems, or multicompartmentalized structures, which mimic the hierarchical architecture of cells, the artificial beta-cells disclosed herein are self-regulated, which can effectively sense external changes in glucose levels, process internal 'signal transduction' and 'exocytose' insulin as a feedback. Of particular significance, by spatially equipping the vesicles-in-vesicle superstructures with a medically relevant enzymatic cascade system and membrane fusion machinery, the synthetic artificial cells disclosed herein are the first which recreate the stimuli-responsive vesicle fusion-mediated 'exocytosis' process, which further guides the evolution of synthetic cells. Such artificial cells will provide new models to study other biological processes. Moreover, the self-regulated design principle can also be applied for designing other, more complicated artificial cells for replacement of other cell deficiencies such as neurological diseases, and immunological disorders.

The AβCs are novel treatments for diseases such as diabetes. Based on rational design, the AβC precisely controlled blood glucose levels in a normal range for a long term. More importantly, it efficiently avoided a potential risk to hypoglycemia compared to previous pH-sensitive materials. To date, most reported glucose oxidase-based glucose-responsive insulin delivery systems mainly utilized matrices consisting of pH-sensitive materials, which can be either swelling/shrinking or degraded under hyperglycemic status in an uncontrollable way once induced. In the present AβCs, protons generated by glucose oxidation are the signal mediator to induce PEG shield detachment from insulin-loaded ISVs and made the peptide on ISVs sterically unshielded. After that, random collision of ISVs with the outer membrane to induce peptide interactions sustained a low level of the fusion process for several hours and avoided hypoglycemia. By confining all biochemical processes in well-isolated microenvironments delineated by lipids, fast responsiveness was achieved both in vitro and in vivo. Moreover, based on the reversible nature of pH-tuned PEG attachment and detachment, pulsatile insulin release in response to graded glucose concentrations could run for numerous cycles, thereby withstanding blood glucose fluctuations that are significant features of even well-controlled type 1 and type 2 diabetes.

The AβCs are biocompatible. Owning to host rejection of transplanted cells and the extensive immunosuppressive therapy needed to address it, and limited amounts of donor cells, the clinical application of beta-cell transplantation has been limited. In contrast, the artificial beta-cells are easily fabricated in labs and simply 'transplanted' subcutaneously within e.g., a thermogel, thereby avoiding the use of immunosuppressive drug. Due to the biocompatible and biodegradable properties of the materials used, all the transplanted components were completely degraded within 4 weeks with no noticeable inflammatory region or fibrotic encapsulation.

Synthetic AβCs recapitulate the key functions of β cells, including sensing glucose levels, internally transducing signals and dynamically secreting insulin via vesicle fusion. Several differences exist between AβCs and natural β cells. Natural β cells are electrically excitable and leverage variations in membrane potential to couple fluctuations in blood glucose levels to stimulation or inhibition of insulin secretion. In contrast, the glucose sensing and stimulated insulin exocytosis inside AβCs are simplified into pH-tuned dynamic processes within confined microenvironments. Furthermore, natural β cells secrete insulin via a biphasic process (a rapid first phase and prolonged second phase) to maintain a baseline insulin release at all times. In AβCs, the random collision of the insulin-containing ISVs with the outer membrane to induce peptide interactions made a low level of the fusion process sustainable for several hours. Related to this, the AβCs do not show burst insulin release that has been reported in conventional pH-responsive materials, conferring protection against potentially life-threatening insulin-induced hypoglycemia. Moreover, based on the reversible nature of pH-tuned PEG attachment and detachment, pulsatile insulin release in response to graded glucose concentrations can run for numerous cycles, thereby withstanding the blood glucose fluctuations that are significant features of even well-controlled type 1 and type 2 diabetes. One of the greatest advantages of the AβCs is that they can be 'transplanted' directly within e.g., an injectable gel or potential transcutaneous microneedle patches to restore blood glucose homeostasis, thereby avoiding use of the immunosuppressive drugs required for live cells transplant. Results presented here show that automated dynamic control of blood glucose concentrations to the near-normal range is feasible with synthetic artificial cells.

From a broad view, by loading different functional proteins or hormones insides the ISLs, synthetic cells for treating different cellular functional deficiencies can be readily fabricated. Also, by changing the glucose metabolism enzymes inside the OLV with other enzymes or enzymatic systems having different disease-related signal molecules as substrates, diverse synthetic cells can be obtained for curing different diseases. Moreover, besides utilizing pH-responsive DNA bridges to control the anchoring and detachment of the PEG shield, other stimulus-responsive functional groups that can respond to light, temperature or magnetic field can also be introduced into this system to build smart synthetic cells. In addition to utilizing coiled-coil formation peptides to trigger membrane fusion, other mechanisms such as host-guest supramolecular interaction, zipper DNA duplex formation, and electrostatic interaction can be employed to pull the membranes of ISV and OLV close together and promote membrane fusion.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is therefore intended that the appended claims cover all such equivalent variations that fall within the spirit and scope of the invention.

We claim:

1. A particle comprising:
    an inner liposomal vesicle (ILV) encapsulating insulin or a biologically active compound derived from insulin;
    an outer liposomal vesicle (OLV) encapsulating the ILV;
    a membrane fusion-promoting agent, wherein said membrane fusion-promoting agent selectively facilitates membrane fusion in response to changes in pH within the particle; and
    a pH-altering agent, wherein said pH-altering agent is a glucose-responsive enzyme inside the OLV but not inside an ILV.

2. The particle of claim 1, wherein the membrane fusion-promoting agent promotes fusion between the ILV and the OLV.

3. The particle of claim 1, wherein the membrane fusion-promoting agent comprises a SNARE polypeptide.

4. The particle of claim 1, wherein the membrane fusion-promoting agent comprises a Peptide-K, a Peptide-E, or combinations thereof.

5. The particle of claim 1, wherein the membrane fusion-promoting agent comprises a first membrane fusion-promoting agent attached to the OLV and a second membrane fusion-promoting agent attached to the ILV.

6. The particle of claim 1, wherein the pH-altering agent reduces the pH inside the OLV in response to glucose.

7. The particle of claim 1, wherein the glucose-responsive enzyme comprises a glucose oxidase.

8. The particle of claim 1, wherein the OLV further comprises a glucose membrane transporter.

9. The particle of claim 8, wherein the glucose membrane transporter transports glucose into the OLV.

10. The particle of claim 8, wherein the glucose membrane transporter comprises a Glucose Transporter 2 (GLUT2) polypeptide.

11. The particle of claim 1, wherein the OLV further comprises a proton transporter.

12. The particle of claim 11, wherein the proton transporter transports protons out of the OLV.

13. The particle of claim 11, wherein the proton transporter comprises a Gramicidin A polypeptide.

14. The particle of claim 1, wherein the particle further comprises a peroxide-metabolizing enzyme.

15. The particle of claim 14, wherein the peroxide-metabolizing enzyme comprises a catalase (CAT) polypeptide.

16. The particle of claim 1, wherein the ILV further comprises a membrane fusion-inhibiting agent which shields access to the membrane fusion-promoting agent.

17. The particle of claim 16, wherein the membrane fusion-inhibiting agent comprises a polyethylene glycol (PEG) molecule.

18. The particle of claim 16, wherein the polyethylene glycol (PEG) molecule comprises an acid-degradable polyethylene glycol (PEG) molecule.

19. A medicament comprising the particle of claim 1 and a pharmaceutically acceptable excipient.

* * * * *